US010117927B2

(12) United States Patent
Kim et al.

(10) Patent No.: US 10,117,927 B2
(45) Date of Patent: Nov. 6, 2018

(54) MEDIUM COMPOSITION FOR PREPARING BOTULINUM TOXIN

(71) Applicant: DAEWOONG CO., LTD., Gyeonggi-do (KR)

(72) Inventors: Kyoung-Yun Kim, Jeollabuk-do (KR); Hye-Young Sul, Gyeonggi-do (KR); Kyoung-Min Min, Gangwon-do (KR)

(73) Assignee: DAEWOONG CO., LTD., Gyeonggi-Do (KR)

( * ) Notice: Subject to any disclaimer, the term of this patent is extended or adjusted under 35 U.S.C. 154(b) by 25 days.

(21) Appl. No.: 15/521,833

(22) PCT Filed: Apr. 28, 2016

(86) PCT No.: PCT/KR2016/004431
§ 371 (c)(1),
(2) Date: Apr. 25, 2017

(87) PCT Pub. No.: WO2016/175566
PCT Pub. Date: Nov. 3, 2016

(65) Prior Publication Data
US 2017/0252431 A1    Sep. 7, 2017

(30) Foreign Application Priority Data

Apr. 28, 2015    (KR) .......................... 10-2015-0059655

(51) Int. Cl.
*A61K 39/385*    (2006.01)
*A61K 39/39*    (2006.01)
*C12N 1/20*    (2006.01)

(52) U.S. Cl.
CPC ............ *A61K 39/385* (2013.01); *A61K 39/39* (2013.01); *C12N 1/20* (2013.01)

(58) Field of Classification Search
None
See application file for complete search history.

(56) References Cited

U.S. PATENT DOCUMENTS

| | | | |
|---|---|---|---|
| 2005/0069562 A1 | 3/2005 | Donovan | |
| 2005/0238668 A1 | 10/2005 | Wang et al. | |
| 2009/0017074 A1* | 1/2009 | Maitre-Wilmotte | ........................ A61K 39/102 424/256.1 |
| 2012/0237497 A1 | 9/2012 | Wegman | |

FOREIGN PATENT DOCUMENTS

| | | |
|---|---|---|
| EP | 2133415 A1 | 12/2009 |
| GB | 790521 | 2/1958 |
| JP | 2009297028 A | 12/2009 |
| JP | 2014083054 A | 5/2014 |
| KR | 10-2009-0120222 A | 11/2009 |
| KR | 10-1339349 B1 | 12/2013 |
| WO | WO0001840 A1 | 1/2000 |
| WO | 0105997 A2 | 1/2001 |
| WO | WO2005038009 A2 | 4/2005 |
| WO | WO2006042542 A2 | 4/2006 |
| WO | WO2009142352 A1 | 11/2009 |
| WO | WO2011008713 A1 | 1/2011 |

OTHER PUBLICATIONS

Fang et al. 2009 (Production of Clostridium difficile toxin in a medium totally free of both animal and dairy proteins or digests; PNAS, 106(32):13225-13229).*
Vera 1944 (A Comparative Study of Materials Suitable for the Cultivation of Clostridia; Journal of Bacteriology; vol. XLVII, pp. 59-69) (Year: 1944).*
Fang et al. 2009 (Production of Clostridium difficile toxin in a medium totally free of both animal and dairy proteins of digests; PNAS 106(32): 13225-13229): (Year: 2009)*
Binz, T., et al., "The Complete Sequence of Botulinum Neurotoxin Type A and Comparision with Other Clostridial Neurotoxins", "The Journal of Biological Chemistry", Jun. 5, 1990, pp. 9153-9158, vol. 265, No. 16.
Fang, A., et al., "Production of Clostridium difficile toxin in a medium totally free of both animal and dairy proteins or digests", "Proceedings of the National Academy of Sciences", Aug. 11, 2009, pp. 13225-13229, vol. 106, No. 32.
Gessler, F., "A new scaleable method for the purification of botulinum neurotoxin type E", "Journal of Biotechnology", Mar. 29, 2005, pp. 204-211, vol. 119.
Montecucco, C., et al., "Tetanus and botulism neurotoxins: a new group of zinc proteases", "Trends in Biochemical Sciences", Sep. 1993, pp. 324-327, vol. 18, No. 9.

(Continued)

*Primary Examiner* — Mary Maille Lyons
(74) *Attorney, Agent, or Firm* — Hultquist, PLLC; Steven J. Hultquist

(57) ABSTRACT

The present invention relates to a medium composition for production of botulinum toxin and, more particularly, to a medium composition for culture of *Clostridium* sp. capable of producing botulinum toxin. The medium composition of the present invention comprises a casein hydrolysate and at least one plant-derived peptone selected from the group consisting of a garden pea hydrolysate, a cotton seed hydrolysate and a wheat gluten hydrolysate. When the medium according to the present invention, which contains plant-derived peptones, casein hydrolysates and minerals, is used for culture of *Clostridium botulinum*, the growth rate of the bacterium in the medium is higher than that in each of the medium that is in current use and the medium comprising plant-derived peptones alone. In addition, when the medium of the present invention is used, a high concentration of botulinum toxin can be produced by culturing the bacterium in a safe manner.

9 Claims, 23 Drawing Sheets
(23 of 23 Drawing Sheet(s) Filed in Color)

(56) References Cited

OTHER PUBLICATIONS

Park, M.K., et al., "Binding of Clostridium botulinum type B toxin to rat brain synaptosome", "FEMS Microbiology Letters", Jun. 18, 1990, pp. 243-248, vol. 72.

Poulain, B., et al., "Neurotransmitter release is blocked intracellularly by botulinum neurotoxin, and this requires uptake of both toxin polypeptides by a process mediated by the larger chain", "Proceedings of the National Academy at Sciences", Jun. 1988, pp. 4090-4094, vol. 85.

Pruisner, S.B., "Creutzfeldt-Jakob Disease and Scrapie Prions", "Alzheimer Disease and Associated Disorders", 1989, pp. 52-78, vol. 31, No. 1/2.

Schantz, E.J., et al., "Properties and Use of Botulinum Toxin and Other Microbial Neurotoxins in Medicine", "Microbiological Review", Mar. 1992, pp. 80-99, vol. 56, No. 1.

Simpson, L.L., "Molecular Pharmacology of Botulinum Toxin and Tetanus Toxin", "Annual Review of Pharmacology and Toxicology", 1986, pp. 427-453, vol. 26.

Sugiyama, H., "Clostridium botulinum Neurotoxin", "Microbiological Reviews", Sep. 1980, pp. 419-448, vol. 44, No. 3.

Note: For the non-patent literature citations that no month of publication is indicated, the year of publication is more than 1 year prior to the effective filing date of the present application.

"Nitrogen source for medium addition", "New Products", 2009, p. 25 vol. 77, No. 3.

"Nitrogen source for medium addition", "New Products", 2009, Page(s) Eng Trans, vol. 77, No. 3.

\* cited by examiner

| Types of Medium | 1 (APF Medium Candidate) | 2 (APF Medium Candidate) | 3 (APF Medium Candidate) | 4 (APF Medium Candidate) | 5 (APF Medium Candidate) | 6 (APF Medium Candidate) |
|---|---|---|---|---|---|---|
| |  | | | | | |
| Precipitation | | ○ | ○ | ○ | ○ | |
| Types of Medium | 7 (APF Medium Candidate) | 8 (APF Medium Candidate) | 9 (APF Medium Candidate) | 10 (APF Medium Candidate) | 11 (APF Medium Candidate) | 12 (APF Medium Candidate) |
| |  | | | | | |
| Precipitation | ○ | | | | ○ | |

Fig. 5

| Types of Medium | 1 (APF Medium Candidate) | 2 (APF Medium Candidate) | 3 (APF Medium Candidate) | 4 (APF Medium Candidate) | 5 (APF Medium Candidate) | 6 (APF Medium Candidate) |
|---|---|---|---|---|---|---|
| Growth | × | ○ | × | ○ | ○ | ○ |
| Types of Medium | 7 (APF Medium Candidate) | 8 (APF Medium Candidate) | 9 (APF Medium Candidate) | 10 (APF Medium Candidate) | 11 (APF Medium Candidate) | 12 (APF Medium Candidate) |
| Growth | × | × | × | × | × | ○ |

Fig. 6

| Types of Medium | 1 (APF Medium Candidate) | 2 (APF Medium Candidate) | 3 (APF Medium Candidate) | 4 (APF Medium Candidate) | 5 (APF Medium Candidate) | 6 (APF Medium Candidate) | 7 (APF Medium Candidate) | 8 (APF Medium Candidate) | 9 (APF Medium Candidate) | 10 (APF Medium Candidate) | 11 (APF Medium Candidate) | 12 (APF Medium Candidate) | 13 (APF Medium Candidate) |
|---|---|---|---|---|---|---|---|---|---|---|---|---|---|
| Growth | O | O | O | O | O | O | O | O | O | O | O | X | X |

(A)

(B)

MEDIUM COMPOSITION FOR PREPARING BOTULINUM TOXIN

CROSS-REFERENCE TO RELATED APPLICATIONS

This application is a U.S. national phase under the provisions of 35 U.S.C. § 371 of International Patent Application No. PCT/KR2016/004431 filed Apr. 28, 2016, which in turn claims priority of Korean Patent Application No. 10-2015-0059655 filed Apr. 28, 2015. The disclosures of such international patent application and Korean priority patent application are hereby incorporated herein by reference in their respective entireties, for all purposes.

TECHNICAL FIELD

The present invention relates to a medium composition for production of botulinum toxin and, more particularly, to a medium composition for culture of *Clostridium* sp. capable of producing botulinum toxin. The medium composition of the present invention comprises a casein hydrolysate and at least one plant-derived plant-derived peptone selected from the group consisting of a garden pea hydrolysate, a cotton seed hydrolysate and a wheat gluten hydrolysate.

BACKGROUND ART

A variety of *Clostridium* sp. that secrete neurotoxic toxins have been discovered since 1890s, and the characterization of toxins that are secreted from these bacteria has been made for the past 70 years (Schant, E. J. et al., *Microbiol. Rev.*, 56:80, 1992).

Neurotoxic toxins derived from the *Clostridium* sp., that is, botulinum toxins, are classified into seven serotypes (types A to G) depending on their serological properties. Each of the toxins has a toxin protein having a size of about 150 kDa and naturally comprises a complex of several non-toxic proteins bound thereto. A medium complex (300 kDa) is composed of a toxin protein and a non-toxic non-hemagglutinin protein, and a large complex (450 kDa) and a very large complex (900 kDa) are composed of the medium-sized complex bound to hemagglutinin (Sugiyama, H., *Microbiol. Rev.*, 44:419, 1980). Such non-toxic hemagglutinin proteins are known to function to protect the toxin from low pH and various proteases in the intestines.

The toxin is synthesized as a single polypeptide having a molecular weight of about 150 kDa in cells, and then cleaved at a position of ⅓ starting from the N-terminal end by the action of intracellular protease or treatment with an artificial enzyme such as trypsin into two units: a light chain (L; molecular weight: 50 kDa) and a heavy chain (H; molecular weight: 100 kDa). The cleaved toxin has greatly increased toxicity compared to the single polypeptide. The two units are linked to each other by a disulfide bond and have different functions. The heavy chain binds to a receptor of a target cell (Park. M. K. et al., *FEMS Microbiol. Lett.*, 72:243, 1990) and functions to interact with a biomembrane at low pH (pH 4) to form a channel (Mantecucco, C. et al., *TIBS.*, 18:324, 1993), and the light chain has the pharmacological activity of interfering the secretion of neurotransmitters, when it is permeable to cells by using detergent or introduced by electroporation or etc (Poulain, B. et al., *Proc. Natl. Acad. Sci. USA.*, 85:4090, 1988).

The toxin inhibits the exocytosis of acetylcholine at the cholinergic presynapse of a neuromuscular junction to cause asthenia. It has been considered that even treatment with a very small amount of the toxin exhibits toxicity, suggesting that the toxin has any enzymatic activity (Simpson, L. L. et al., *Ann. Rev. Pharmacol. Toxicol.*, 26:427, 1986).

According to a recent report, the toxin has metallopeptidase activity, and its substrates include composed of synaptobrevin, syntaxin, a synaptosomal associated protein of 25 kDa (SNAP25), etc., which are the unit proteins of an exocytosis machinery complex. Each type of toxin uses one of the above-described three proteins as its substrate, and it is known that type B, D, F and G toxins cleave synaptobrevin at a specific site, type A and E toxins cleave SNAP25 at a specific site, and type C cleaves syntaxin at a specific site (Binz, T. et al., *J. Biol. Chem.*, 265:9153, 1994).

Particularly, type A botulinum toxin is known to be soluble in a dilute aqueous solution at a pH of 4.0-6.8. It is known that a stable non-toxic protein is separated from neurotoxin at a pH of about 7 or higher, and as a result, the toxicity is gradually lost. Particularly, it is known that the toxicity decreases as pH and temperature increase.

The botulinum toxin is fatal to the human body even in small amounts and is easy to produce in large amounts. Thus, it constitutes four major bio-terror weapons together with *Bacillus anthracis, Yersinia pestis* and smallpox virus. However, it was found that, when type A botulinum toxin is injected at a dose that does not systematically affect the human body, it can paralyze local muscle in the injected site. Based on this characteristic, type A botulinum toxin can be used in a wide range of applications, including wrinkle removing agents, agents for treating spastic hemiplegia and cerebral palsy, etc. Thus, the demand for type A botulinum toxin has increased, and studies on methods of producing botulinum toxin so as to satisfy the demand have been actively conducted.

A current typical commercial product is BOTOX® (a purified neurotoxin complex of type A botulinum toxin) that is commercially available from Allergan, Inc., USA. A 100-unit vial of BOTOX® is composed of about 5 ng of a purified neurotoxin complex of type A botulinum toxin, 0.5 mg of human serum albumin and 0.9 mg of sodium chloride and is reconstituted using sterile saline without a preservative (injection of 0.9% sodium chloride). Other commercial products include Dysport® (a complex of *Clostridium botulinum* type A toxin and hemagglutinin, which has lactose and human serum albumin in a pharmaceutical composition comprising botulinum toxin and is reconstituted using 0.9% sodium chloride before use) that is commercially available from Ipsen Ltd., UK, MyoBloc® (an injectable solution (a pH of about 5.6) comprising botulinum type B toxin, human serum albumin, sodium succinate and sodium chloride) that is commercially available from Solstice Neurosciences, Inc.

A medium for culture of *Clostridium botulinum*, which is generally used in a method for production of botulinum toxin as disclosed in Korean Patent No. 10-1339349, comprises animal components. Thus, if an animal abnormal prion known as an agent that causes transmissible spongiform encephalopathy is contained in the animal components due to contamination, it poses problems in a process for producing botulinum toxin.

Transmissible spongiform encephalopathy (TSE) is known as a neurodegenerative disorder causing serious degeneration of neurons, and examples thereof includes bovine spongiform encephalopathy (BSE), Scrapie, Creutzfeldt-Jakob disease (CJD), Gerstmann-Straussler-Scheinker syndrome, Kuru, transmissible mink encephalopathy, chronic wasting disease, feline spongiform encephalopathy, etc., which affect humans and animals. It was reported that BSE crosses the species barrier and infects even humans.

The agent that causes transmissible spongiform encephalopathy (TSE) has characteristics in that it has no immunogenicity and the incubation period is long. From histopathological analysis of BSE-affected bovine brain tissue, it can be seen that special spongiform vacuoles were formed in the brain due to damage to neurons and deposition of abnormal protein fibers.

The cause of TSE is a proteinaceous infectious particle known as the abnormal prion. Unlike general viruses that require nucleic acid, the abnormal prion is an infectious particle composed of protein alone without containing nucleic acid. Regarding TSE, it is known that, when an abnormal prion (PrPsc) that is an infectious particle binds to a normal prion (PrPc), it is converted to a pathogenic prion which is then accumulated in the brain (Prusiner SB, *Alzheimer Dis Assoc Disord.*, 3:52-78, 1989).

Creutzfeldt-Jakob disease is a rare neurodegenerative disorder of human transmissible spongiform encephalopathy (TSE) where the transmissible agent is apparently an abnormal isoform of a prion protein. An individual with Creutzfeldt-Jacob disease can deteriorate from apparent perfect health to akinetic mutism within six months. Thus, a potential risk may exist of acquiring a prion mediated disease, such as Creutzfeldt-Jacob disease, from the administration of a pharmaceutical composition which comprises a biologic, such as a botulinum toxin, obtained using animal-derived products. Thus, if a pharmaceutical composition is prepared by drug substance produced using animal-derived components, it can subject the patient to a potential risk of receiving various pathogens or infectious agents.

Under this technical background, the present inventors have found that, when a medium comprising transmissible spongiform encephalopathy (TSE)-free plant-derived peptone, mineral components and TSE-free casein hydrolysate (e.g., TSE-certificated casein hydrolysate) is used for culture of *Clostridium botulinum* in order to prevent the risk of developing the above-described prion-mediated disease, the risk of development of the prion-mediated disease that can occur in a medium that is in current use (original medium) can be excluded, and the growth rate of *Clostridium botulinum* in the medium can be increased compared to that in the medium that is in current use and the plant-derived peptone-containing medium, thereby completing the present invention.

DISCLOSURE OF INVENTION

Technical Problem

It is an object of the present invention to provide a medium composition comprising a plant-derived peptone having no risk of transmissible spongiform encephalopathy (TSE) infection and a casein hydrolysate having no risk of TSE infection, and a method for production of botulinum toxin, which improves the production of botulinum toxin by culturing *Clostridium botulinum* in the medium composition.

Technical Solution

To achieve the above object, the present invention provides a medium composition for culture of *Clostridium botulinum*, the medium composition comprising: at least one plant-derived peptone selected from the group consisting of a garden pea hydrolysate, a cotton seed hydrolysate and a wheat gluten hydrolysate; and a casein hydrolysate.

The present invention also provides a method for producing botulinum toxin, comprising the steps of: (a) culturing *Clostridium botulinum* using the medium composition to produce botulinum toxin; and (b) recovering the produced botulinum toxin.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5 shows the growth of *Clostridium botulinum* in media obtained by additionally adding vitamins, amino acids and "BD Recharge™ without Glucose and L-Glutamine" to media for culture of the bacterium, which contain plant-derived peptones and minerals.

FIG. 6 shows the growth of *Clostridium botulinum* in media for culture of the bacterium, which contain various kinds of plant-derived peptones.

FIG. 7 shows contour plots of FFD for mineral screening, and response optimization.

FIG. 8 shows contour plots of FFD for mineral screening, and response optimization.

FIG. 9 shows contour plots for plant peptone screening, and response optimization.

FIG. 11 shows contour plots for a culture medium at 24 hours after inoculation of *Clostridium botulinum* into a medium comprising plant-derived peptones to which a casein hydrolysate has been added.

BEST MODE FOR CARRYING OUT THE INVENTION

Figure 1:
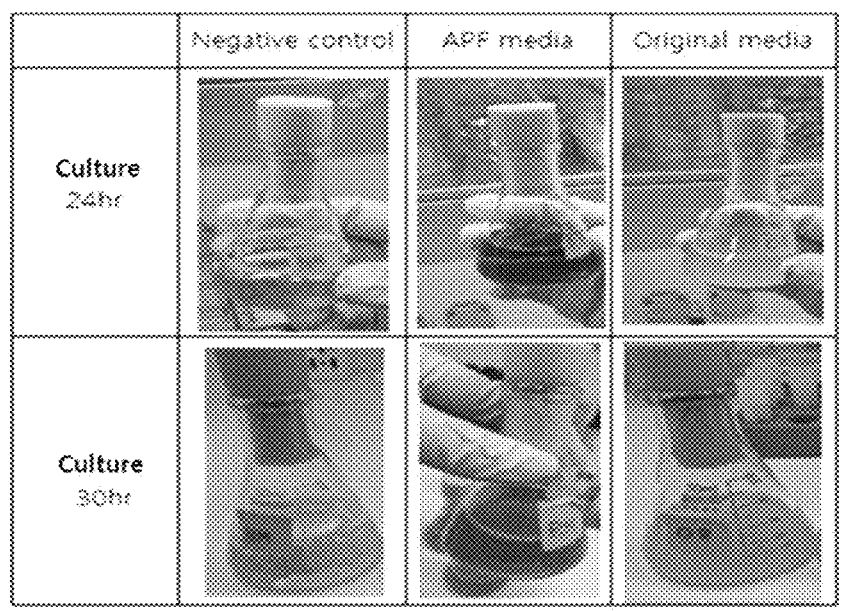
FIG. 1 shows the growth of *Clostridium botulinum* in a medium (APF medium) comprising plant-derived peptone.

In the present invention, an animal protein-free (APF) medium composition showed an increased growth rate of *Clostridium botulinum* compared to a medium that is in current use (original medium), but it was taken into account to add medium components that further increase the growth rate of the bacterium and have no risk of infection with TSE or the like. Thus, a casein hydrolysate (e.g., a TSE-certificated casein hydrolysate), which has not been reported to cause TSE infection, was added to the APF medium, and the growth of the bacterium in the APF medium was examined. As a result, the APF medium showed an increased growth rate of the bacterium compared to a medium that is in current use and a medium comprising plant-derived peptones alone. Thus, if the above medium is used, a high concentration of botulinum toxin can be produced by culturing a bacterium in a safe manner under TSE-free conditions.

As used herein, the term "medium that is in current use or original medium" means a medium comprising casein hydrolysate, yeast extract and thioglycollate medium, which are animal-derived medium components. The term "APF medium (animal protein-free medium)" means a medium that contains no animal-derived protein and that contains plant-derived peptones, minerals and glucose.

In an example of the present invention, in order to produce botulinum toxin by culturing *Clostridium botulinum* under transmissible spongiform encephalopathy (TSE)-free conditions, an APF medium comprising TSE-free plant-derived peptone was prepared and compared with a medium that is in current use (containing an animal component). As a result, it could be seen that an optimal medium composition for culturing *Clostridium botulinum* is one comprising a plant-derived peptone, at least one mineral selected from the group consisting of $KH_2PO_4$, $K_2HPO_4$ and $Na_2HPO_4$, and a carbon source (e.g., glucose, and the optimal growth of the bacterium in this medium was found. As a result, as shown in Table 13, it was determined that the optimal contents of plant-derived peptones in the finally selected medium composition for culture of *Clostridium botulinum* are 5 g/L Hy-Pea™ 7404, 10 g/L UltraPep™ Cotton and 5 g/L HyPep™ 4601N, and the optimal contents of minerals in the medium composition are 5.5 g/L $K_2HPO_4$ and 3 g/L $Na_2HPO_4$.

In another example of the present invention, the growth pattern of *Clostridium botulinum* in the finally selected APF medium comprising plant-derived peptones and minerals and the toxin concentration were measured. As a result, as shown in Table 12 and FIG. 10, the OD value started to increase after 12 hours of culture of *Clostridium botulinum*, and at 24 hours of culture, the culture medium showed an $OD_{540nm}$ of 3.5465 and an $OD_{600nm}$ of 3.0695. Then, the OD value decreased gradually, and at 48 hours of culture, the culture medium showed an $OD_{540}$ of 0.792 and an $OD_{600nm}$ of 0.7224. The toxin concentration in the culture supernatant of *Clostridium botulinum* started to increase after 5 hours of culture and showed a final value of 31.41 µg/ml. When the toxin concentration was measured after rupturing the bacterium, the toxin started to be produced after 5 hours of culture, and the toxin concentration continued to increase, was maintained at a uniform level after 28 hours of culture, and showed a final value of 38.39 µg/ml.

In another example of the present invention, the growth pattern of *Clostridium botulinum* in a medium containing plant-derived peptones and casein hydrolysate was examined. As a result, as shown in Table 17 and FIG. 15, a medium that is in current use showed an increase in the growth rate after 24 hours of culture of *Clostridium botulinum* and showed the peak $OD_{540nm}$ value of 3.384 at 39 hours of culture. An APF medium containing plant-derived peptones showed an increase in the growth rate after 18 hours of culture and showed a peak $OD_{540nm}$ value of 3.526 at 28 hours of culture.

In addition, a plant-derived peptone-containing APF medium+casein hydrolysate showed an increase in the growth rate after 18 hours of culture and showed a peak $OD_{540nm}$ value of 5.628 at 26 hours of culture. Thus, the $OD_{540nm}$ value at 24 hours of culture was compared, the medium that is in current use showed an $OD_{540nm}$ value of 1.2382, the plant-derived peptone-containing APF medium showed an $OD_{540nm}$ value of 2.8595, and the plant-derived peptone-containing APF medium+casein hydrolysate showed an $OD_{540nm}$ value of 5.244. Thus, the OD value of the plant-derived peptone-containing APF medium+casein hydrolysate at 24 hours of culture was about 4.23 times higher than that of the medium that is in current use and about 1.83 times higher than that of the plant-derived peptone-containing APF medium. And the peak OD value of the plant-derived peptone-containing APF medium+casein hydrolysate was about 1.6 times higher than that of the plant-derived peptone-containing APF medium.

As shown in Table 18, it was determined that the optimal contents of plant-derived peptones in the finally selected medium composition for culture of *Clostridium botulinum*, which contains a transmissible spongiform encephalopathy (TSE)-free casein hydrolysate, are 5 g/L Hy-Pea™ 7404, 10 g/L UltraPep™ Cotton and 5 g/L HyPep™ 4601N, and the optimal contents of minerals in the medium composition are 5.5 g/L $K_2HPO_4$ and 3 g/L $Na_2HPO_4$, and the contents of the casein hydrolysates are 20 g/L N-Z-Amine A and 11 g/L N-Z-Case TT.

Based on this, in one aspect, the present invention is directed to a medium composition for culture of *Clostridium botulinum*, the medium composition comprising: at least one plant-derived peptone selected from the group consisting of a garden pea hydrolysate, a cotton seed hydrolysate and a wheat gluten hydrolysate; and a casein hydrolysate.

As used herein, the term "plant-derived peptone" means a peptone extracted from garden pea, cotton seed or wheat gluten. Preferably, the plant-derived peptone may be commercially available Hy-Pea™ 7404, UltraPep™ Cotton, HyPep™ 7504 or HyPep™ 4601N, but is not limited thereto. The term "casein hydrolysate" means a component extracted from milk Preferably, the casein hydrolysate may be a casein hydrolysate containing about 85.5-94.5 wt % of peptides having a molecular weight of 500 Da or less, or a casein hydrolysate containing about 63.56-70.25 wt % of peptides having a molecular weight of 500 Da or less. More preferably, the casein hydrolysate may be commercially available N-Z-Amine A or N-Z-Case TT, but is not limited thereto.

As used herein, the term "plant-derived peptone" or "plant-derived hydrolysate" means a product obtained by degrading a protein isolated from a plant. For example, the garden pea peptone (garden pea hydrolysate) means a product obtained by degrading a total protein isolated from garden pea. In addition, the term "casein hydrolysate" means a product obtained by degrading casein protein.

Degradation of the plant-derived protein or the casein protein is preferably performed by partial digestion. Degradation of the protein is preferably performed by acid treatment, base treatment, enzyme treatment, high-pressure treatment, heat treatment or physical treatment. More preferably, the plant-derived peptone or the casein hydrolysate may be one obtained by enzyme treatment. The physical treatment is, for example, grinding.

The plant-derived peptone or casein hydrolysate that is used in the present invention is a partial degradation product of protein, is a mixture comprising not only amino acids that are single molecules, but also peptides composed of several to several tens of amino acids, and intact protein molecules.

In the present invention, the content of the plant-derived peptone in the medium composition may be 0.1-10 w/v % (1-100 g/L), preferably 0.2-5 w/v % (2-50 g/L), more preferably 0.5-2 w/v % (5-20 g/L).

In the present invention, the medium composition contains all the garden pea hydrolysate, the cotton seed hydrolysate and the wheat gluten hydrolysate, and the content ratio of the garden pea hydrolysate, the cotton seed hydrolysate and the wheat gluten hydrolysate in the medium composition may be 1:0.24-43.62:0.01-50.57 by weight, preferably 1:0.68-14.46:0.09-9.87 by weight, more preferably 1:1.6-2.4:0.6-1.4 by weight.

In the present invention, the content of the casein hydrolysate in the medium composition may be 0.22-15.5 w/v % (2.2-155 g/L), preferably 0.44-7.75 w/v % (4.4-77.5 g/L), more preferably 1.1-3.1 w/v % (11-31 g/L).

In the present invention, the casein hydrolysate may be a hydrolysate containing about 85.5-94.5 wt % of peptides having a molecular weight of 500 Da or less and/or a hydrolysate containing about 63.56-70.25 wt % of peptides having a molecular weight of 500 Da or less.

In the present invention, the casein hydrolysate comprises both a hydrolysate containing about 85.5-94.5 wt % of peptides having a molecular weight of 500 Da or less and a hydrolysate containing about 63.56-70.25 wt % of peptides having a molecular weight of 500 Da or less, and the content ratio of the hydrolysate containing about 85.5-94.5 wt % of peptides having a molecular weight of 500 Da or less and the hydrolysate containing about 63.56-70.25 wt % of peptides having a molecular weight of 500 Da or less may be 0.01-40:0.01-22 by weight, preferably 10-30:5.5-16.5 by weight, more preferably 16-24:8.8-13.2 by weight.

In the present invention, the medium composition for culture of *Clostridium botulinum* may further contains a carbon source and at least one mineral selected from the group consisting of $K_2HPO_4$ (dipotassium phosphate), $Na_2HPO_4$ (disodium phosphate) and $KH_2PO_4$ (monopotassium phosphate).

Herein, examples of the carbon source include, but are not limited to, monosaccharides (e.g., glucose, fructose, etc.), disaccharides (e.g., maltose, sucrose, etc.), oligosaccharides, polysaccharides (e.g., dextrin, cyclodextrin, starch, etc.), sugar alcohols (e.g., xylitol, sorbitol, erythritol, etc.).

In the present invention, the content of the mineral in the medium composition may be 0.05-3.5 w/v %(0.5-35 g/L), preferably 0.1-1.75 w/v % (1-17.5 g/L), and more preferably 0.25-0.7 w/v % (2.5-7 g/L).

In another aspect, the present invention is directed to a method for producing botulinum toxin, comprising the steps of: (a) culturing *Clostridium botulinum* using the above-described medium composition to produce botulinum toxin; and (b) recovering the produced botulinum toxin.

In the present invention, the culturing may be performed under anaerobic conditions, and the botulinum toxin may be selected from the group consisting of botulinum toxin types A, B, C, D, E, F and G.

EXAMPLES

Hereinafter, the present invention will be described in further detail with reference to examples. It will be obvious to a person having ordinary skill in the art that these examples are illustrative purposes only and are not to be construed to limit the scope of the present invention. Thus, the substantial scope of the present invention will be defined by the appended claims and equivalents thereof.

Example 1: Culture of *Clostridium botulinum* in Plant-Derived Peptone Medium 1-1: Composition of a Medium Currently Used in Culture The reagents and medium components used in the present invention were purchased from Sigma (USA), Kerry Inc. (USA), BD Biosciences (USA), Gibco Life Technologies (USA), and Quest (USA).

A medium that is in current use having a composition comprising 2% casein hydrolysate (20 g/L), 1% yeast extract (10 g/L), 1% glucose (10 g/L) and 0.5% thioglycollate medium (5 g/L) was used for the seed culture and main culture of *Clostridium botulinum* to produce botulinum toxin. 5 g of the thioglycollate medium per liter of the medium that is in current use is composed of 2.52 g of an enzymatic digest of casein, 0.84 g of yeast extract, 0.925 g of dextrose, 0.085 g of sodium thioglycollate, 0.42 g of NaCl, 0.085 g of L-cysteine, 0.00014 g of Resazurin and 0.125 g of bacteriological agar.

1-2: Composition of APF Medium Used in Culture

A negative control medium was prepared by removing casein hydrolysate, yeast extract and thioglycollate medium from the medium that is in current use (original medium) for culture of *Clostridium botulinum*, and an animal protein-free (APF) medium was prepared by adding four plant-derived peptone candidates (Hy-Pea™ 7404, UltraPep™ Cotton, HyPep™ 7504, and HyPep™ 4601N) to the negative control medium (Table 1).

Table 1 shows the components of the plant-derived peptone-containing APF medium for culture of *Clostridium botulinum* in comparison with the medium that is in current use.

TABLE 1

| Components of Medium | Conc. (g/L) | medium that is in current use | Negative Control | APF Medium |
|---|---|---|---|---|
| Glucose | 10 | 10 | 10 | 10 |
| Sodium Chloride (NaCl) | 0.42 | 0.42 | 0.42 | 0.42 |
| Casein hydrolysate | 20 | 20 | — | — |
| Yeast extract | 10 | 10 | — | — |
| Thioglycollate medium | 5 | 5 | — | — |
| Hy-Pea ™ 7404 | 20 | — | — | 20 |
| UltraPep ™ Cotton | 10 | — | — | 10 |
| HyPep ™ 7504 | 10 | — | — | 10 |
| HyPep ™ 4601N | 10 | — | — | 10 |

1-3: Seed Culture of *Clostridium botulinum*

20 µl of *Clostridium botulinum* (the Korean Centers for Disease Control and Prevention Accession No.: 4-029-CBB-IS-001) was inoculated into a culture tube containing 10 ml of a sterile medium having each of the compositions described in Examples 1-1 and 1-2 and was subjected to primary seed culture (stationary culture) at 35° C. for 22-30 hours under anaerobic conditions. When the growth of the bacterium in the primary seed culture was confirmed, 8 ml of the primary seed culture was inoculated into a 1-liter culture bottle containing 800 ml of a sterile medium having the same medium composition and was subjected to secondary seed culture (stationary culture) at 35° C. for 8-15 hours under anaerobic conditions.

1-4: Main Culture of *Clostridium botulinum*

In order to produce a botulinum toxin by culturing *Clostridium botulinum*, the main culture of the bacterium was performed. Specifically, 9.3 L of a medium having each of the compositions described in Examples 1-1 and 1-2 was prepared and placed in a 10-liter incubator, followed by sterilization of the medium. Nitrogen was supplied to make anaerobic conditions, and the growth of the bacterium was performed at a temperature of 35° C. and an agitation speed of 50 rpm.

The secondary seed culture in the 1-liter culture bottle in Example 1-3 was inoculated into a 10-liter incubator through an inoculation line connected to the inoculation port of the 10-liter incubator. *Clostridium botulinum* in the 10-liter incubator was cultured under the conditions of 35° C. and 50 rpm and the set culture conditions were monitored and recorded. When the bacterium was cultured for 100 hours or more, the main culture was terminated.

The growth of *Clostridium botulinum* in the animal protein-free (APF) medium prepared by adding four types of plant-derived peptone candidates (Hy-Pea™ 7404, Ultra-Pep™ Cotton, HyPep™ 7504, and HyPep™ 4601N) to the negative control medium was compared with that of the bacterium in the negative control medium prepared by removing casein hydrolysate, yeast extract and thioglycollate medium from the medium that is in current use (original medium) (Table 1).

As a result, as shown in Table 1 and FIG. 1, *Clostridium botulinum* did not grow in the negative control medium, but started to grow in the original medium (medium that is in current use) at 24 hours after inoculation of the bacterium and started to grow in the plant-derived peptone-containing medium at 30 hours after inoculation of the bacterium.

Example 2: Culture of *Clostridium botulinum* in Medium Containing Plant-Derived Peptone, Mineral, Amino Acid and Vitamin Because the growth of *Clostridium botulinum* in the medium prepared by adding four plant-derived peptones in Example 1 was slower than that in the original medium, solutions thereto were provided as follows.

1) To examine the effect of thioglycollate functioning to make anaerobic conditions, thioglycollate was removed from the original medium (medium that is in current use), and a change in the growth rate of the bacterium in the thioglycollate-free medium was analyzed.

2) Because the slower growth rate could be because of the lack of the nitrogen source, the peptone concentration in the medium used for culture of the bacterium was increased two times.

3) The growth of *Clostridium botulinum* in a medium obtained by adding mineral, amino acid and vitamin to the plant-derived peptone-containing medium was compared with the growth of *Clostridium botulinum* in an APF medium disclosed in U.S. Pat. No. 8,012,716 (Allergan) (Table 2).

Table 2 shows the components of the medium for culture of *Clostridium botulinum*, which contains plant-derived peptones, minerals, amino acids and vitamins.

TABLE 2

| Components of Medium | g/L | medium that is in current use | 1 (APF Medium Candidate) | 2 (APF Medium Candidate) | 3 (APF Medium Candidate) | 4 (APF Medium Candidate) | APF Medium of Allergan Company |
|---|---|---|---|---|---|---|---|
| Glucose | 10 | 10 | 10 | 10 | 10 | 10 | 15 |
| Sodium Chloride (NaCl) | 0.42 | 0.42 | 0.42 | 0.42 | 0.42 | 0.42 | — |
| Casein hydrolysate | 20 | 20 | 20 | — | — | — | — |
| Yeast extract | 10 | 10 | 10 | — | — | — | 12 |
| Thioglycollate medium | 5 | 5 | — | — | — | — | — |
| Hy-Pea™ 7404 | 20 | — | — | 20 | 40 | 20 | — |
| UltraPep™ Cotton | 10 | — | — | 10 | 20 | 10 | — |
| HyPep™ 7504 | 10 | — | — | 10 | 20 | 10 | — |
| HyPep™ 4601N | 10 | — | — | 10 | 20 | 10 | — |
| $KH_2PO_4$ | 7 | — | — | — | — | 7 | — |
| $K_2HPO_4$ | 5.5 | — | — | — | — | 5.5 | — |
| $Na_2HPO_4$ | 5 | — | — | — | — | 5 | — |
| $MgSO_4 7H_2O$ | 10 | — | — | — | — | 10 | — |
| Vitamin Kit 100X | | — | — | — | — | 1X | — |
| Amino acid mixture 50X | | — | — | — | — | 1X | — |
| Soy peptone | 32.5 | — | — | — | — | — | 32.5 |

Figure 2:
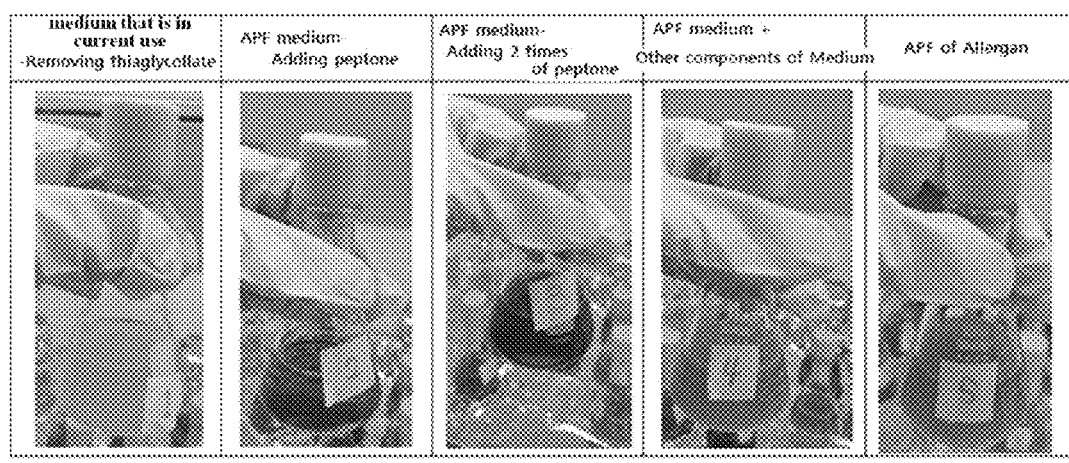
FIG. 2 shows the growth of *Clostridium botulinum* in a medium comprising plant-derived peptones, minerals, amino acids and vitamins.

As a result, as shown in Table 2 and FIG. 2, when the bacterium was cultured in the medium that is in current use without thioglycollate, the growth rate of the bacterium in the medium was slower than that in the thioglycollate-containing medium, indicating that thioglycollate influences the growth rate of the bacterium. When the peptone concentration in the medium was increased two times, the bacterium did not grow in the medium. When in the case in which mineral components, amino acids and vitamins were added to the peptone-containing medium, the growth rate of the bacterium was similar to that in the medium that is in current use, but a precipitate was formed after sterilization of the medium. In addition, it was seen that the growth rate of the bacterium in the Allergan's APF medium was similar to that in the medium that is in current use.

Example 3: Production of Precipitate by Sterilization of Medium Containing Plant-Derived Peptones, Minerals, Amino Acid and Vitamin In Example 2, it was observed that the growth rate of *Clostridium botulinum* in the medium containing plant-derived peptones, minerals, amino acids and vitamins, among the APF medium candidates 2 to 4 shown in Table 2, was similar that in the medium that is in current use. However, formation of a precipitate appeared after sterilization of the medium, and thus the cause thereof was examined (Table 3).

Table 3 shows the components of a medium for culture of *Clostridium botulinum*, which was used in sterilization and contains plant-derived peptones, minerals, amino acids and vitamins.

TABLE 3

| Components of Medium | g/L | medium that is in current use | 1 (APF Medium Candidate) | 2 (APF Medium Candidate) | 3 (APF Medium Candidate) | 4 (APF Medium Candidate) |
|---|---|---|---|---|---|---|
| Glucose | 10 | 10 | 10 | 10 | 10 | 10 |
| Sodium Chloride (NaCl) | 0.5 | 0.5 | 0.5 | 0.5 | 0.5 | 0.5 |
| Casein hydrolysate | 20 | 20 | — | — | — | — |
| Yeast extract | 10 | 10 | — | — | — | — |
| Thioglycollate medium | 5 | 5 | — | — | — | — |
| Hy-Pea ™ 7404 | 20 | — | 20 | 20 | 20 | 20 |
| UltraPep ™ Cotton | 10 | — | 10 | 10 | 10 | 10 |
| HyPep ™ 7504 | 10 | — | 10 | 10 | 10 | 10 |
| HyPep ™ 4601N | 10 | — | 10 | 10 | 10 | 10 |
| $KH_2PO_4$ | 7 | — | 7 | 7 | — | — |
| $K_2HPO_4$ | 5.5 | — | 5.5 | 5.5 | — | — |
| $Na_2HPO_4$ | 5 | — | 5 | 5 | — | — |
| $MgSO_4 7H_2O$ | 10 | — | 10 | 10 | — | — |
| Vitamin Kit 100X | | — | 1X | — | 1X | 1X (Adding after Sterilization) |
| Amino acid mixture 50 X | | — | 1X | — | 1X | 1X (Adding after Sterilization) |

Figure 3:
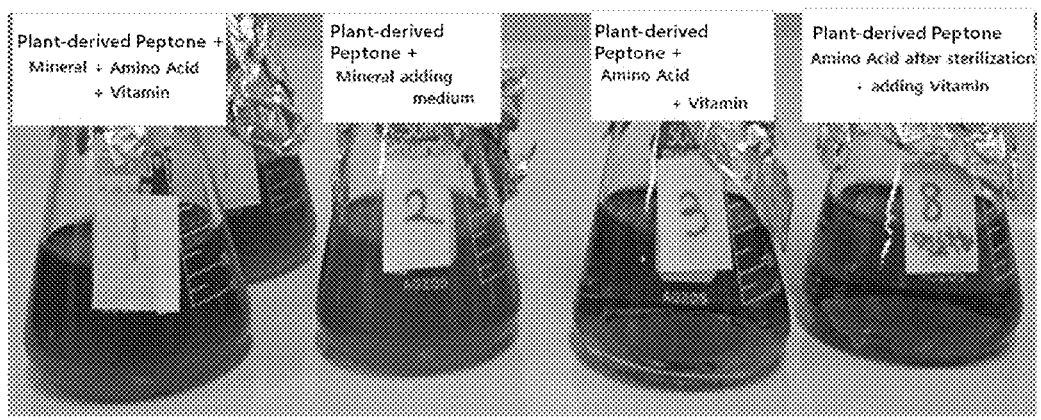
FIG. 3 shows the results of examining whether a precipitate is formed after sterilization of a medium comprising plant-derived peptones, minerals, amino acids and vitamins.

As a result, as shown in Table 3 and FIG. 3, only in the case in which minerals were added to the plant-derived peptone-containing medium, a precipitate was formed after sterilization of the medium, indicating that the main cause of formation of the precipitate was the minerals. This is believed to be because the mineral components interacted with one another under the conditions of high temperature and high pressure during sterilization of the medium.

Example 4: Formation of Precipitate by Sterilization of Medium Containing Plant-Derived Peptones and Minerals In order to identify the mineral components involved in the formation of precipitate caused by sterilization as confirmed in Example 3, various combinations of different components were added to media, followed by sterilization (Table 4).

Table 4 shows the components of media for culture of *Clostridium botulinum*, which contain plant-derived peptones and minerals, and the results of sterilization of the media.

TABLE 4

| Components of Medium | g/L | medium that is in current use | 1 (APF Medium Candidate) | 2 (APF Medium Candidate) | 3 (APF Medium Candidate) | 4 (APF Medium Candidate) | 5 (APF Medium Candidate) | 6 (APF Medium Candidate) | 7 (APF Medium Candidate) | 8 (APF Medium Candidate) | 9 (APF Medium Candidate) | 10 (APF Medium Candidate) | 11 (APF Medium Candidate) | 12 (APF Medium Candidate) |
|---|---|---|---|---|---|---|---|---|---|---|---|---|---|---|
| Glucose | 10 | 10 | 10 | 10 | 10 | 10 | 10 | 10 | 10 | 10 | 10 | 10 | 10 | 10 |
| Sodium Chloride (NaCl) | 0.5 | 0.5 | 0.5 | 0.5 | 0.5 | 0.5 | 0.5 | 0.5 | 0.5 | 0.5 | 0.5 | 0.5 | 0.5 | 0.5 |
| Casein hydrolysate | 20 | 20 | — | — | — | — | — | — | — | — | — | — | — | — |
| Yeast extract | 10 | 10 | — | — | — | — | — | — | — | — | — | — | — | — |
| Thioglycollate medium | 5 | 5 | — | — | — | — | — | — | — | — | — | — | — | — |
| Hy-Pea ™ 7404 | 20 | — | 20 | 20 | 20 | 20 | 20 | 20 | 20 | 20 | 20 | 20 | 20 | 20 |
| UltraPep ™ Cotton | 10 | — | 10 | 10 | 10 | 10 | 10 | 10 | 10 | 10 | 10 | 10 | 10 | 10 |
| HyPep ™ 7504 | 10 | — | 10 | 10 | 10 | 10 | 10 | 10 | 10 | 10 | 10 | 10 | 10 | 10 |
| HyPep ™ 4601N | 10 | — | 10 | 10 | 10 | 10 | 10 | 10 | 10 | 10 | 10 | 10 | 10 | 10 |

TABLE 4-continued

| Components of Medium | g/L | medium that is in current use | 1 (APF Medium Candidate) | 2 (APF Medium Candidate) | 3 (APF Medium Candidate) | 4 (APF Medium Candidate) | 5 (APF Medium Candidate) | 6 (APF Medium Candidate) | 7 (APF Medium Candidate) | 8 (APF Medium Candidate) | 9 (APF Medium Candidate) | 10 (APF Medium Candidate) | 11 (APF Medium Candidate) | 12 (APF Medium Candidate) |
|---|---|---|---|---|---|---|---|---|---|---|---|---|---|---|
| $KH_2PO_4$ | 7 | — | — | 7 | — | 7 | 7 | 7 | — | 7 | 7 | — | — | 10 |
| $K_2HPO_4$ | 5.5 | — | — | 5.5 | 5.5 | — | 5.5 | 5.5 | — | — | 5.5 | 5.5 | 5.5 | — |
| $Na_2HPO_4$ | 5 | — | — | 5 | 5 | 5 | — | 5 | 5 | — | — | 5 | — | 5 |
| $MgSO_4 7H_2O$ | 10 | — | — | 10 | 10 | 10 | 10 | — | 10 | 10 | — | — | 10 | — |
| precipitation, aggregation | | x | ○ | ○ | ○ | ○ | x | ○ | x | x | x | ○ | x | |

Figure 4:
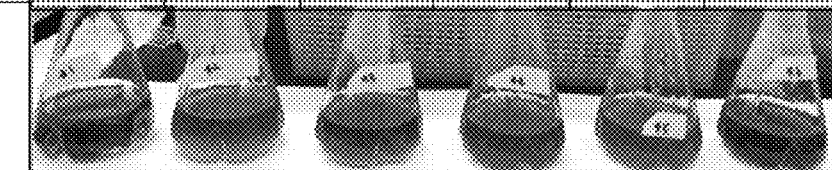
FIG. 4 shows the results of examining whether a precipitate is formed after sterilization of a medium comprising plant-derived peptones and minerals.
Figure 4:
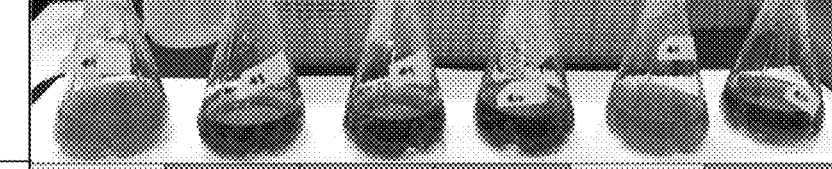
Figure 7A:
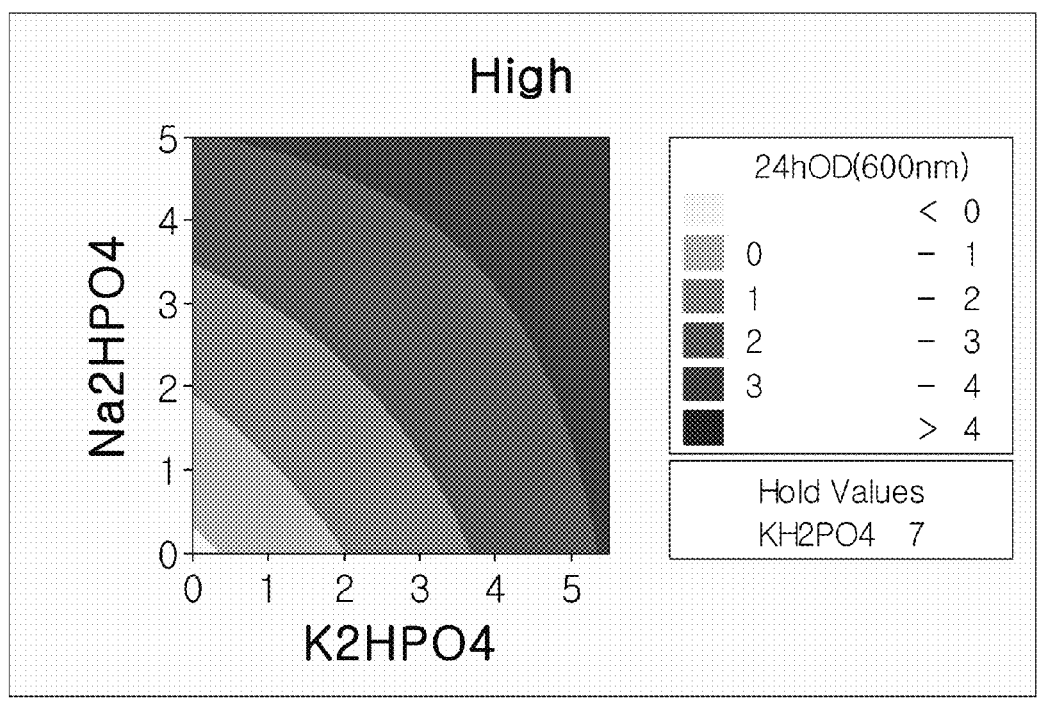
FIG. 7a contour plot for high setting.
Figure 7B:
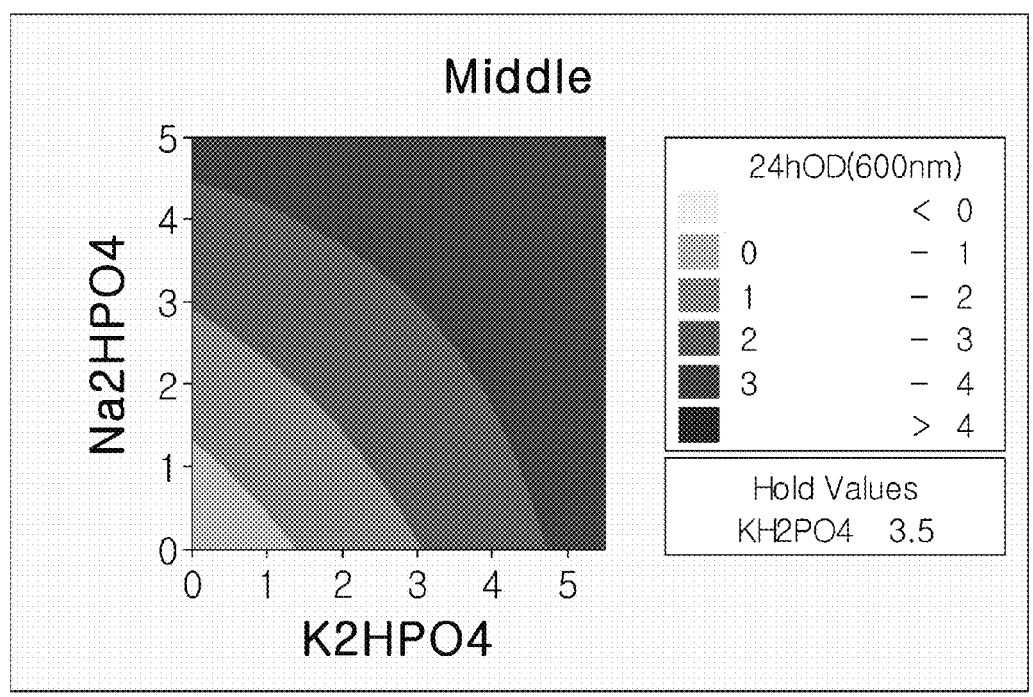
FIG. 7b contour plot for middle setting.
Figure 7C:
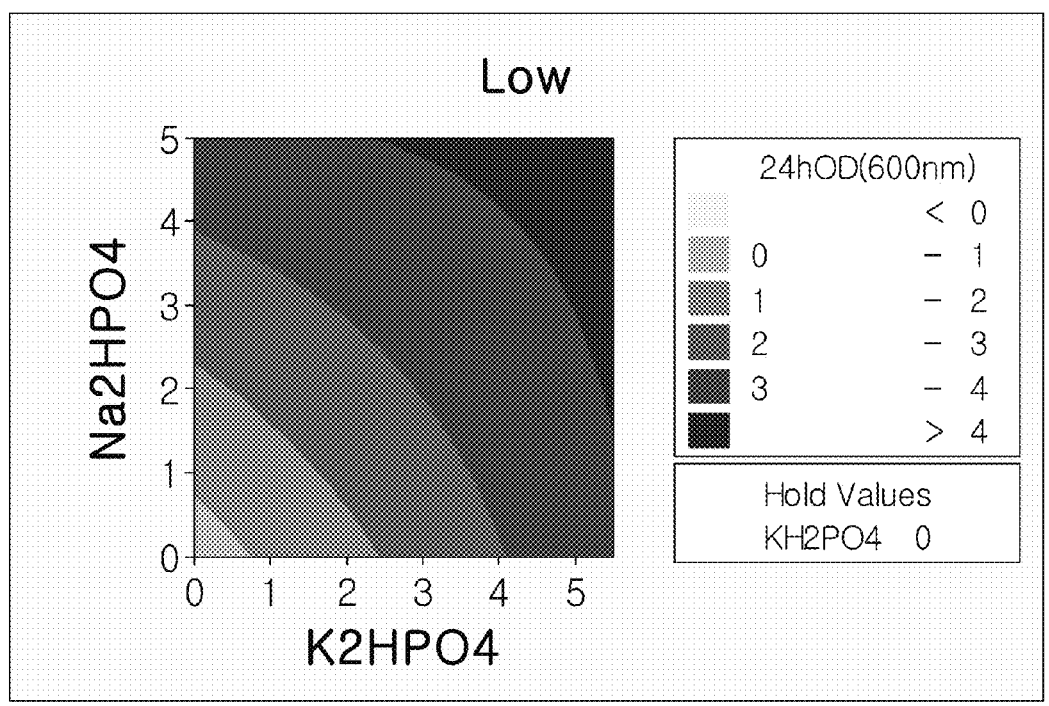
FIG. 7c contour plot for low setting.
Figure 7D:
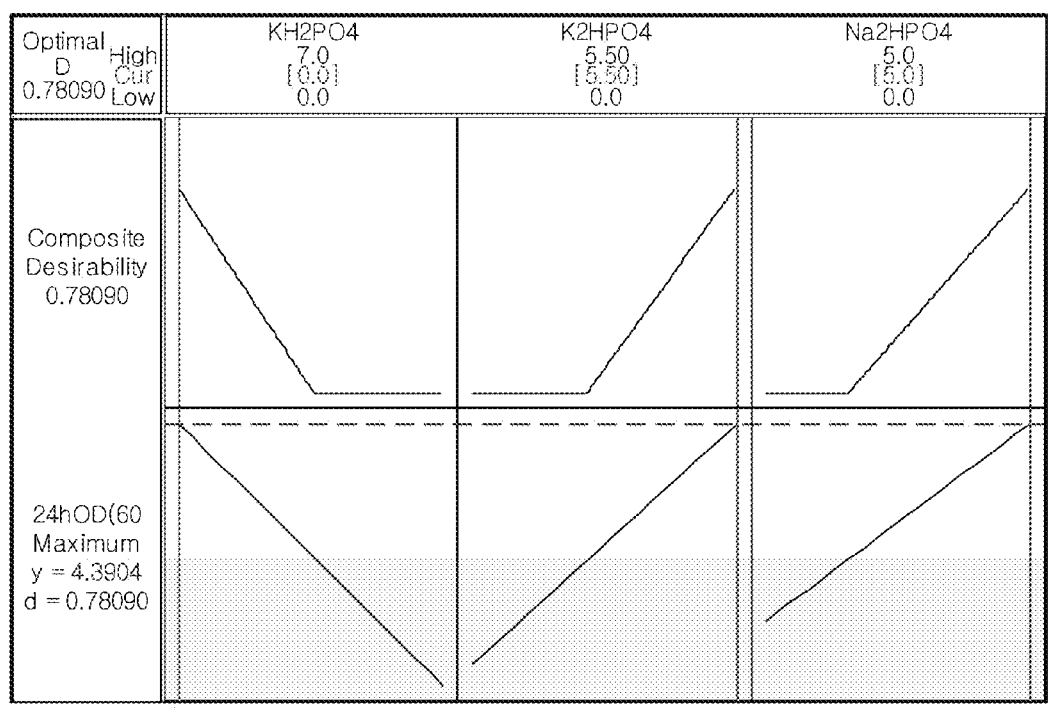
FIG. 7d response optimization for maximum OD.
Figure 8A:
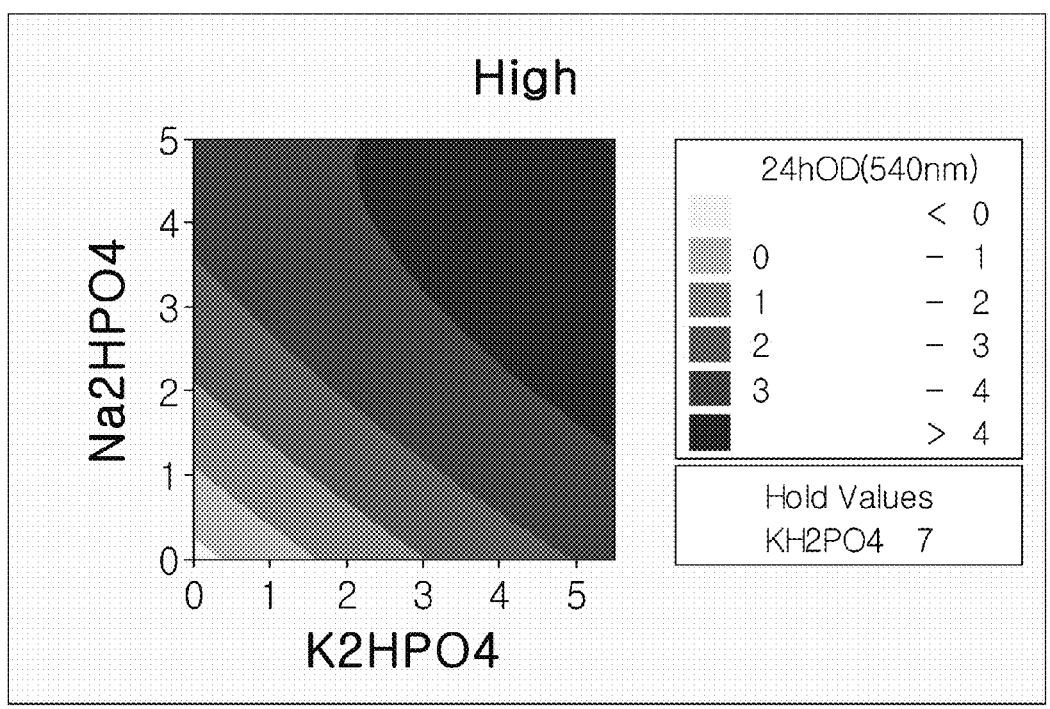
FIG. 8a contour plot for high setting.
Figure 8B:
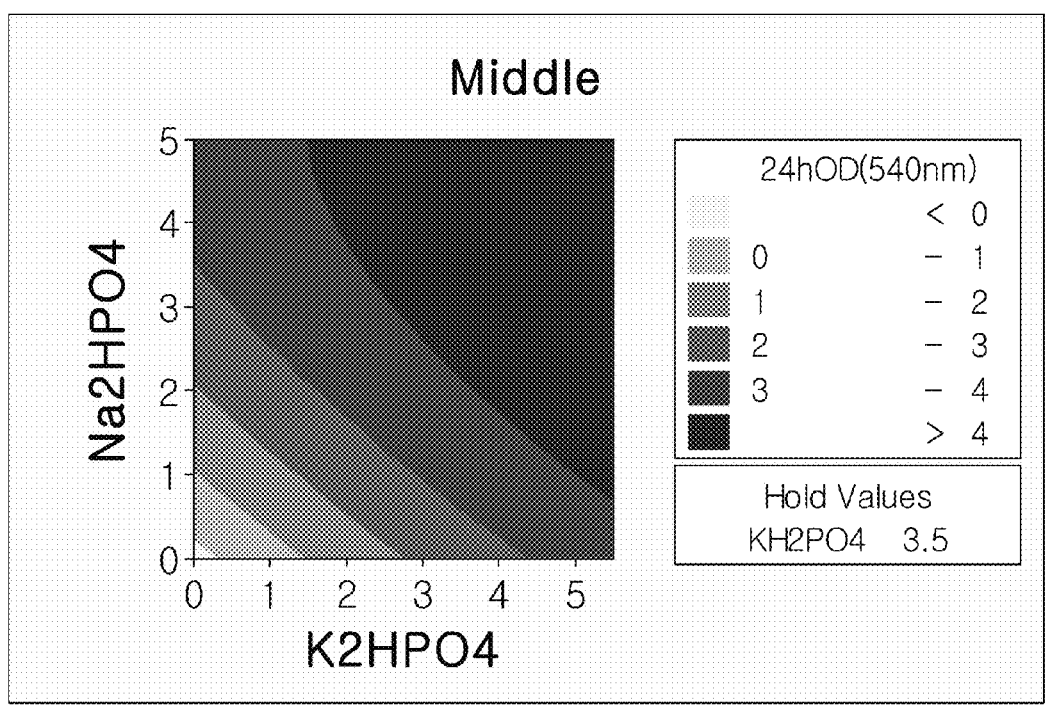
FIG. 8b contour plot for middle setting.
Figure 8C:
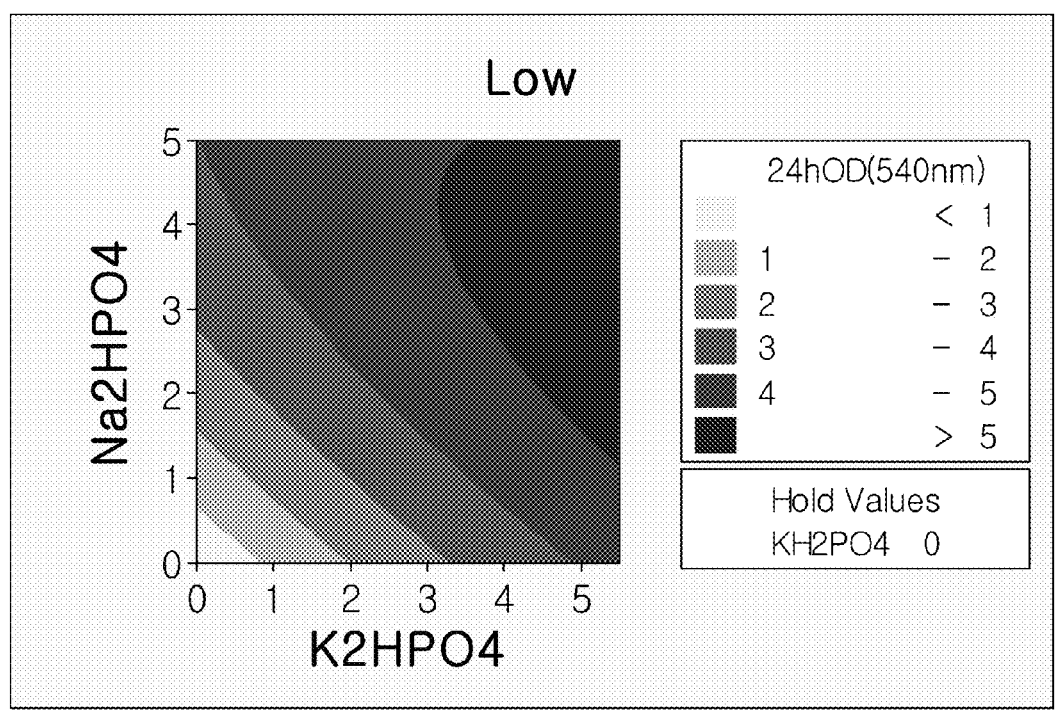
FIG. 8c contour plot for low setting.
Figure 8D:
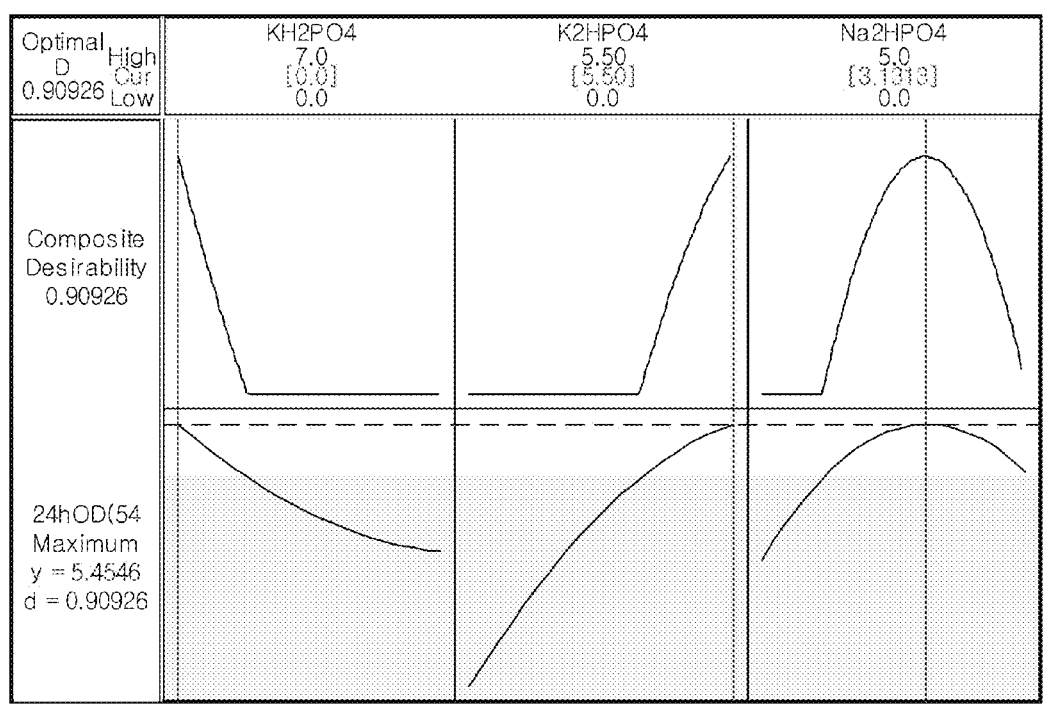
FIG. 8d response optimization for maximum OD.

As a result, as shown in Table 4 and FIG. 4, among the media containing plant-derived peptones and minerals, the medium containing $MgSO_4.7H_2O$ and $K_2HPO_4$ and the medium containing $MgSO_4.7H_2O$ and $Na_2HPO_4$ formed a precipitate after sterilization.

Example 5: Culture of *Clostridium botulinum* Under Conditions in which No Precipitate is Formed in APF Medium An experiment was performed to determine whether culture of *Clostridium botulinum* is possible when vitamin and amino acid are additionally added to the APF medium of Example 4 containing plant-derived peptones and minerals. In addition, an experiment was performed to examine whether culture of the bacterium is possible in a medium which is free of plant-derived peptone and mineral and contains vitamins, amino acids and/or "BD Recharge™ without Glucose and L-Glutamine" (Cat No. 670002, BD Bioscience) (a yeast extract-based medium component free of glucose and L-glutamine) (Table 5).

Table 5 shows the components of media obtained by additionally adding vitamins, amino acids and "BD Recharge™ without Glucose and L-Glutamine" to the medium for culture of *Clostridium botulinum*, which contains plant-derived peptones and minerals, and the growth rates of the bacterium in the media.

TABLE 5

| Components of Medium | g/L | medium that is in current use | 1 (APF Medium Candidate) | 2 (APF Medium Candidate) | 3 (APF Medium Candidate) | 4 (APF Medium Candidate) | 5 (APF Medium Candidate) | 6 (APF Medium Candidate) |
|---|---|---|---|---|---|---|---|---|
| Glucose | 10 | 10 | 10 | 10 | 10 | 10 | 10 | 10 |
| Sodium Chloride (NaCl) | 0.5 | 0.5 | 0.5 | 0.5 | 0.5 | 0.5 | 0.5 | 0.5 |
| Casein hydrolysate | 20 | 20 | — | — | — | — | — | — |
| Yeast extract | 10 | 10 | — | — | — | — | — | — |
| Thioglycollate medium | 5 | 5 | — | — | — | — | — | — |
| Sodium Thioglycollate | 1 | — | — | — | — | — | — | — |
| Hy-Pea ™ 7404 | 20 | — | 20 | 20 | 20 | 20 | 20 | 20 |
| UltraPep ™ Cotton | 10 | — | 10 | 10 | 10 | 10 | 10 | 10 |
| HyPep ™ 7504 | 10 | — | 10 | 10 | 10 | 10 | 10 | 10 |
| HyPep ™ 4601N | 10 | — | 10 | 10 | 10 | 10 | 10 | 10 |
| $KH_2PO_4$ | 7 | — | — | — | 7 | 7 | 7 | — | 7 |
| $K_2HPO_4$ | 5.5 | — | — | 5.5 | — | 5.5 | 5.5 | — |
| $Na_2HPO_4$ | 5 | — | — | 5 | — | — | 5 | 5 |
| $MgSO_4 7H_2O$ | 10 | — | — | — | 10 | — | — | — |
| Vitamin Kit 100X | | — | — | 1X | 1X | 1X | 1X | 1X |
| Amino acid mixture 50 X | | — | — | 1X | 1X | 1X | 1X | 1X |
| w/o Glucose and L-glutamine | 45.42 | — | — | — | — | — | — | — |
| Growth Details | | x | ○ | x | ○ Growing in 24 hrs | ○ Growing in 24 hrs | ○ Growing in 24 hrs | ○ Growing in 24 hrs |

| Components of Medium | 7 (APF Medium Candidate) | 8 (APF Medium Candidate) | 9 (APF Medium Candidate) | 10 (APF Medium Candidate) | 11 (APF Medium Candidate) | 12 (APF Medium Candidate) |
|---|---|---|---|---|---|---|
| Glucose | 10 | 10 | 10 | 10 | 10 | 10 |
| Sodium Chloride (NaCl) | 0.5 | 0.5 | 0.5 | 0.5 | 0.5 | 0.5 |

TABLE 5-continued

| | | | | | | |
|---|---|---|---|---|---|---|
| Casein hydrolysate | — | — | — | — | — | — |
| Yeast extract | — | — | — | — | — | — |
| Thioglycollate medium | — | — | — | — | — | — |
| Sodium Thioglycollate | — | — | 1 | — | — | — |
| Hy-Pea ™ 7404 | 20 | 20 | 20 | 20 | — | — |
| UltraPep ™ Cotton | 10 | 10 | 10 | 10 | — | — |
| HyPep ™ 7504 | 10 | 10 | 10 | 10 | — | — |
| HyPep ™ 4601N | 10 | 10 | 10 | 10 | — | — |
| $KH_2PO_4$ | — | — | — | — | — | — |
| $K_2HPO_4$ | — | — | — | — | — | — |
| $Na_2HPO_4$ | — | — | — | — | — | — |
| $MgSO_4 7H_2O$ | — | — | — | — | — | — |
| Vitamin Kit 100X | 1X | — | — | 1X | — | 1X |
| Amino acid mixture 50 X | 1X | — | — | 1X | — | 1X |
| w/o Glucose and L-glutamine | — | 45.42 | — | 45.42 | 45.42 | 45.42 |
| Growth | x | x | x | x | x | ○ |
| Details | | | | | | Growing in 48 hr |

As a result, as shown in Table 5 and FIG. 5, only in the case in which the medium contained plant-derived peptones and a combination of two or more minerals of $KH_2PO_4$, $K_2HPO_4$ and $Na_2HPO_4$ and further contained vitamin and amino acid, *Clostridium botulinum* grew within 24 hours after inoculation of the bacterium. In addition, in the case in which the medium was free of plant-derived peptone and mineral and contained vitamins, amino acids and "BD Recharge™ without Glucose and L-Glutamine", the bacterium grew within 48 hours after inoculation of the bacterium. In conclusion, the most suitable medium composition for culture of *Clostridium botulinum* comprises plant-derived peptones, $KH_2PO_4$, $K_2HPO_4$, $Na_2HPO_4$, amino acids and vitamins.

Example 6: Culture of *Clostridium botulinum* in Media Containing Different Plant-Derived Peptones An experiment was performed to examine whether culture of *Clostridium botulinum* is possible when different combinations of plant-derived peptones are added to the APF medium of Example 5.

Table 6 shows the components of media for culture of *Clostridium botulinum*, which contain different plant-derived peptones, and the results of examining whether the bacterium grew in the media.

TABLE 6

| Components of Medium | g/L | medium that is in current use | 1 (APF Medium Candidate) | 2 (APF Medium Candidate) | 3 (APF Medium Candidate) | 4 (APF Medium Candidate) | 5 (APF Medium Candidate) | 6 (APF Medium Candidate) |
|---|---|---|---|---|---|---|---|---|
| Glucose | 10 | 10 | 10 | 10 | 10 | 10 | 10 | 10 |
| Sodium Chloride (NaCl) | 0.5 | 0.5 | 0.5 | 0.5 | 0.5 | 0.5 | 0.5 | 0.5 |
| Casein hydrolysate | 20 | 20 | — | — | — | — | — | — |
| Yeast extract | 10 | 10 | — | — | — | — | — | — |
| Thioglycollate medium | 5 | 5 | — | — | — | — | — | — |
| Sodium thioglycollate | 0.1 | — | — | — | — | — | — | — |
| Hy-Pea ™ 7404 | 10 | — | 10 | 10 | — | — | — | — |
| UltraPep ™ Cotton | 10 | — | 10 | — | 10 | — | — | — |
| HyPep ™ 7504 | 10 | — | 10 | — | — | 10 | — | 10 |
| HyPep ™ 4601N | 10 | — | 10 | — | — | — | 10 | 10 |
| $KH_2PO_4$ | 7 | — | 7 | 7 | 7 | 7 | 7 | 7 |
| $K_2HPO_4$ | 5.5 | — | 5.5 | 5.5 | 5.5 | 5.5 | 5.5 | 5.5 |
| $Na_2HPO_4$ | 5 | — | 5 | 5 | 5 | 5 | 5 | 5 |
| $MgSO_4 7H_2O$ | 10 | — | — | — | — | — | — | — |
| Vitamin Kit 100X | | — | — | 1X | 1X | 1X | 1X | 1X |
| Amino acid mixture 50 X | | — | — | 1X | 1X | 1X | 1X | 1X |
| w/o Glucose and L-glutamine | | 45.42 | — | — | — | — | — | — |
| Growth | | | ○ | ○ | ○ | ○ | ○ | ○ |

TABLE 6-continued

| Components of Medium | 7 (APF Medium Candidate) | 8 (APF Medium Candidate) | 9 (APF Medium Candidate) | 10 (APF Medium Candidate) | 11 (APF Medium Candidate) | 12 (APF Medium Candidate) | 13 (APF Medium Candidate) |
|---|---|---|---|---|---|---|---|
| Glucose | 10 | 10 | 10 | 10 | 10 | 10 | 10 |
| Sodium Chloride (NaCl) | 0.5 | 0.5 | 0.5 | 0.5 | 0.5 | 0.5 | 0.5 |
| Casein hydrolysate | — | — | — | — | — | — | — |
| Yeast extract | — | — | — | — | — | — | — |
| Thioglycollate medium | — | — | — | — | — | — | — |
| Sodium thioglycollate | — | — | — | — | — | 0.1 | — |
| Hy-Pea ™ 7404 | — | — | 10 | 10 | 10 | — | — |
| UltraPep ™ Cotton | 10 | 10 | — | — | 10 | — | — |
| HyPep ™ 7504 | — | 10 | — | 10 | — | — | — |
| HyPep ™ 4601N | 10 | — | 10 | — | — | — | — |
| $KH_2PO_4$ | 7 | 7 | 7 | 7 | 7 | — | 7 |
| $K_2HPO_4$ | 5.5 | 5.5 | 5.5 | 5.5 | 5.5 | — | 5.5 |
| $Na_2HPO_4$ | 5 | 5 | 5 | 5 | 5 | — | 5 |
| $MgSO_4 7H_2O$ | — | — | — | — | — | — | — |
| Vitamin Kit 100X | 1X | 1X | 1X | 1X | 1X | 1X | 1X |
| Amino acid mixture 50 X | 1X | 1X | 1X | 1X | 1X | 1X | 1X |
| w/o Glucose and L-glutamine | — | — | — | — | — | 45.42 | 45.42 |
| Growth | ○ | ○ | ○ | ○ | ○ | x | x |

As a result, as shown in Table 6 and FIG. 6, even when only or two of the four plant-derived peptones were added to the medium, culture of *Clostridium botulinum* was possible.

Taking the results of Examples 5 and 6 into account, it could be seen that at least one plant-derived peptone should be contained in the medium and that the plant-derived peptone cannot be substituted with "BD Recharge™ without Glucose and L-Glutamine" (Cat No. 670002, BD Bioscience) (a yeast extract-based medium component free of glucose and L-glutamine 7.

Example 7: Experiment for Selection of Two of Three Minerals Contained in Medium In Examples 1 to 7, it was determined that the APF medium composition used for culture of *Clostridium botulinum* comprises glucose, sodium chloride (NaCl), four plant-derived peptones, three minerals, amino acids, and vitamins. Among these medium components, medium components having no significant effect on the growth of the bacterium were removed to reduce the number of the medium components. Thus, it was judged that amino acids and vitamins have no significant effect on the growth of *Clostridium botulinum*, and under this judgment, amino acids and vitamins were removed from the medium components. In addition, in order to select two of three minerals, the bacterium was cultured using the medium compositions shown in Table 7, and the OD (540 nm and 600 nm) values at 24 hours and 48 hours after inoculation of the bacterium were measured and compared.

Table 7 shows the compositions of media resulting from the first-stage selection of minerals and the growth of *Clostridium botulinum* in the media.

TABLE 7

| Components of Medium | | g/L | medium that is in current use | 1 (APF Medium Candidate) | 2 (APF Medium Candidate) | 3 (APF Medium Candidate) | 4 (APF Medium Candidate) | 5 (APF Medium Candidate) | 6 (APF Medium Candidate) | 7 (APF Medium Candidate) | 8 (APF Medium Candidate) | 9 (APF Medium Candidate) | 10 (APF Medium Candidate) | 11 (APF Medium Candidate) |
|---|---|---|---|---|---|---|---|---|---|---|---|---|---|---|
| Glucose | | 10 | 10 | 10 | 10 | 10 | 10 | 10 | 10 | 10 | 10 | 10 | 10 | 10 |
| Sodium Chloride (NaCl) | | 0.5 | 0.5 | 0.5 | 0.5 | 0.5 | 0.5 | 0.5 | 0.5 | 0.5 | 0.5 | 0.5 | 0.5 | 0.5 |
| Casein hydrolysate | | 20 | 20 | — | — | — | — | — | — | — | — | — | — | — |
| Yeast extract | | 10 | 10 | — | — | — | — | — | — | — | — | — | — | — |
| Thioglycollate medium | | 5 | 5 | — | — | — | — | — | — | — | — | — | — | — |
| Hy-Pea ™ 7404 | | 10 | — | 10 | 10 | 10 | 10 | 10 | 10 | 10 | 10 | 10 | 10 | 10 |
| UltraPep ™ Cotton | | 10 | — | 10 | 10 | 10 | 10 | 10 | 10 | 10 | 10 | 10 | 10 | 10 |
| HyPep ™ 7504 | | 10 | — | 10 | 10 | 10 | 10 | 10 | 10 | 10 | 10 | 10 | 10 | 10 |
| HyPep ™ 4601N | | 10 | — | 10 | 10 | 10 | 10 | 10 | 10 | 10 | 10 | 10 | 10 | 10 |
| $KH_2PO_4$ | | 7 | — | — | — | 7 | — | 7 | — | 7 | — | 7 | 3.5 | 3.5 | 3.5 |
| $K_2HPO_4$ | | 5.5 | — | — | — | — | 5.5 | 5.5 | — | — | 5.5 | 5.5 | 2.75 | 2.75 | 2.75 |
| $Na_2HPO_4$ | | 5 | — | — | — | — | — | — | 5 | 5 | 5 | 5 | 2.5 | 2.5 | 2.5 |
| Culture 24 hr OD | 540 nm | | 0.942 | −0.017 | −0.024 | 4.396 | 3.226 | 4.218 | 3.214 | 4.964 | 3.991 | 3.951 | 3.938 | 3.594 |
| | 600 nm | | 0.780 | −0.016 | −0.020 | 3.832 | 2.691 | 3.593 | 2.680 | 4.304 | 3.351 | 3.341 | 3.335 | 3.036 |
| Culture 48 hr OD | 540 nm | | 2.459 | −0.014 | −0.019 | 4.716 | 5.220 | 3.502 | 5.460 | 2.056 | 2.603 | 5.726 | 5.682 | 5.434 |
| | 600 nm | | 2.057 | −0.015 | −0.018 | 3.852 | 4.288 | 2.989 | 4.480 | 1.587 | 2.020 | 4.688 | 4.647 | 4.459 |

As a result, as shown in Table 7, at 24 hours of inoculation of the bacterium, the medium that is in current use showed an OD (540 nm) value of 0.942, and the APF medium containing $K_2HPO_4$ and $Na_2HPO_4$ showed the highest OD (540 nm) value of 4.964 among the APF media. In addition, at 48 hours after inoculation of the bacterium, the APF medium containing $KH_2PO_4$ and $Na_2HPO_4$ showed the highest OD value and active bacterial growth.

Meanwhile, as shown in FIGS. 7a to 7d, contour plots of $K_2HPO_4$ and $Na_2HPO_4$ having high main effects were drawn. As a result, as the concentrations of $K_2HPO_4$ and $Na_2HPO_4$ increased, the OD value increased. And *Clostridium botulinum* showed the highest growth when minerals were added to the medium at the concentrations of $KH_2PO_4$=0 g/L, $K_2HPO_4$=5.5 g/L, and $Na_2HPO_4$=5 g/L.

Meanwhile, in order to confirm the results of bacterial culture according to more precise addition of minerals, a second-stage experiment was performed using response surface methodology. Because the medium composition cannot have a negative value, the experiment was planned using a CCF (central composite faced) design and performed by culturing the bacterium in the medium compositions shown in Table 8. Then, the experimental results were combined with the results of the previously performed FFD and subjected to statistical analysis.

Table 8 shows the compositions of media obtained by the second-stage selection of minerals and the growth of *Clostridium botulinum* in the media.

TABLE 8

| Components of Medium | g/L | 1 (APF Medium Candidate) | 2 (APF Medium Candidate) | 3 (APF Medium Candidate) | 4 (APF Medium Candidate) | 5 (APF Medium Candidate) | 6 (APF Medium Candidate) | 7 (APF Medium Candidate) | 8 (APF Medium Candidate) | 9 (APF Medium Candidate) | medium that is in current use |
|---|---|---|---|---|---|---|---|---|---|---|---|
| Glucose | 10 | 10 | 10 | 10 | 10 | 10 | 10 | 10 | 10 | 10 | 10 |
| Sodium Chloride (NaCl) | 0.5 | 0.5 | 0.5 | 0.5 | 0.5 | 0.5 | 0.5 | 0.5 | 0.5 | 0.5 | — |
| Casein hydrolysate | 20 | — | — | — | — | — | — | — | — | — | 20 |
| Yeast extract | 10 | — | — | — | — | — | — | — | — | — | 10 |
| Thioglycollate medium | 5 | — | — | — | — | — | — | — | — | — | 5 |
| Hy-Pea™ 7404 | 10 | 10 | 10 | 10 | 10 | 10 | 10 | 10 | 10 | 10 | — |
| UltraPep™ Cotton | 10 | 10 | 10 | 10 | 10 | 10 | 10 | 10 | 10 | 10 | — |
| HyPep™ 7504 | 10 | 10 | 10 | 10 | 10 | 10 | 10 | 10 | 10 | 10 | — |
| HyPep™ 4601N | 10 | 10 | 10 | 10 | 10 | 10 | 10 | 10 | 10 | 10 | — |
| $KH_2PO_4$ | 7 | — | 7 | 3.5 | 3.5 | 3.5 | 3.5 | 3.5 | 3.5 | 3.5 | — |
| $K_2HPO_4$ | 5.5 | 2.75 | 2.75 | — | 5.5 | 2.75 | 2.75 | 2.75 | 2.75 | 2.75 | — |
| $Na_2HPO_4$ | 5 | 2.5 | 2.5 | 2.5 | 2.5 | — | 5 | 2.5 | 2.5 | 2.5 | — |
| OD 24 hr | 540 nm | 4.408 | 3.587 | 2.233 | 4.639 | 1.778 | 4.332 | 3.904 | 3.907 | 4.046 | 1.556 |
|  | 600 nm | 3.836 | 3.086 | 1.896 | 4.068 | 1.503 | 3.777 | 3.366 | 3.368 | 3.505 | 1.307 |
| OD 48 hr | 540 nm | 5.021 | 5.760 | 4.359 | 3.594 | 4.529 | 4.054 | 6.492 | 5.621 | 5.473 | 3.622 |
|  | 600 nm | 4.284 | 4.925 | 3.695 | 3.049 | 3.832 | 3.457 | 5.603 | 4.830 | 4.677 | 3.062 |

Contour plots were drawn and used for comparison. As shown in FIGS. 8a to 8d, the OD value increased as the concentration of $KH_2PO_4$ decreased. When the optimal conditions were compared, the results were different from the results of FFD due to the curvature effect, and the value of $K_2HPO_4$ was the same, but the value of $Na_2HPO_4$ changed from 5 g/L to 3.1313 g/L. Thus, it was confirmed that the optimal mineral conditions of the medium by statistical analysis are 5.5 g/L $K_2HPO_4$ and 3 g/L $Na_2HPO_4$.

Example 8: Experiment for Selection of Plant-Derived Peptones Contained in Medium As shown in Tables 9 and 10, plant-derived peptones were combined according to a mixture design, and the growth of *Clostridium botulinum* in a medium containing the combined plant-derived peptones was examined.

Table 9 shows the compositions of media obtained by the first-stage selection of plant-derived peptones and the growth of *Clostridium botulinum* using the media.

TABLE 9

| Components of Medium | g/L | 1 (APF Medium Candidate) | 2 (APF Medium Candidate) | 3 (APF Medium Candidate) | 4 (APF Medium Candidate) | 5 (APF Medium Candidate) | 6 (APF Medium Candidate) |
|---|---|---|---|---|---|---|---|
| Glucose | 10 | 10 | 10 | 10 | 10 | 10 | 10 |
| Sodium Chloride (NaCl) | 0.5 | 0.5 | 0.5 | 0.5 | 0.5 | 0.5 | 0.5 |

TABLE 9-continued

| | | | | | | | |
|---|---|---|---|---|---|---|---|
| Casein hydrolysate | 20 | — | — | — | — | — | — |
| Yeast extract | 10 | — | — | — | — | — | — |
| Thioglycollate medium | 5 | — | — | — | — | — | — |
| Hy-Pea ™ 7404 | 10 | 5 | 10 | 5 | 5 | — | — |
| UltraPep ™ Cotton | 10 | 5 | — | 5 | 5 | 10 | — |
| HyPep ™ 7504 | 10 | 5 | 10 | 5 | 5 | — | 10 |
| HyPep ™ 4601N | 10 | 5 | — | 5 | 5 | 10 | 10 |
| K$_2$HPO$_4$ | 5.5 | 5.5 | 5.5 | 5.5 | 5.5 | 5.5 | 5.5 |
| Na$_2$HPO$_4$ | 3 | 3 | 3 | 3 | 3 | 3 | 3 |
| OD 24 hr | 540 nm | 3.541 | 2.440 | 3.345 | 3.305 | 3.317 | 2.852 |
| | 600 nm | 3.058 | 2.066 | 2.868 | 2.831 | 2.853 | 2.445 |
| OD 48 hr | 540 nm | 0.811 | 0.935 | 0.731 | 0.799 | 1.400 | 0.777 |
| | 600 nm | 0.714 | 0.795 | 0.647 | 0.694 | 1.199 | 0.680 |

| Components of Medium | | 7 (APF Medium Candidate) | 8 (APF Medium Candidate) | 9 (APF Medium Candidate) | 10 (APF Medium Candidate) | 11 (APF Medium Candidate) | medium that is in current use |
|---|---|---|---|---|---|---|---|
| Glucose | | 10 | 10 | 10 | 10 | 10 | 10 |
| Sodium Chloride (NaCl) | | 0.5 | 0.5 | 0.5 | 0.5 | 0.5 | — |
| Casein hydrolysate | | — | — | — | — | — | 20 |
| Yeast extract | | — | — | — | — | — | 10 |
| Thioglycollate medium | | — | — | — | — | — | 5 |
| Hy-Pea ™ 7404 | | 6.667 | 6.667 | — | — | 10 | — |
| UltraPep ™ Cotton | | 6.667 | 6.667 | 20 | — | 10 | — |
| HyPep ™ 7504 | | — | 6.667 | — | 20 | 10 | — |
| HyPep ™ 4601N | | 6.667 | — | — | — | 10 | — |
| K$_2$HPO$_4$ | | 5.5 | 5.5 | 5.5 | 5.5 | 5.5 | — |
| Na$_2$HPO$_4$ | | 3 | 3 | 3 | 3 | 3 | — |
| OD 24 hr | | 3.695 | 2.772 | 2.353 | 1.688 | 4.842 | 2.239 |
| | | 3.183 | 2.376 | 2.014 | 1.419 | 4.245 | 1.893 |
| OD 48 hr | | 1.660 | 1.090 | 1.810 | 1.402 | 2.093 | 3.341 |
| | | 1.403 | 0.929 | 1.548 | 1.210 | 1.764 | 2.812 |

Table 10 shows the compositions of media obtained by the second-stage selection of plant-derived peptones and the growth of *Clostridium botulinum* using the media.

TABLE 10

| Components of Medium | g/L | 1 (APF Medium Candidate) | 2 (APF Medium Candidate) | 3 (APF Medium Candidate) | 4 (APF Medium Candidate) | 5 (APF Medium Candidate) | 6 (APF Medium Candidate) | 7 (APF Medium Candidate) |
|---|---|---|---|---|---|---|---|---|
| Glucose | 10 | 10 | 10 | 10 | 10 | 10 | 10 | 10 |
| Sodium Chloride (NaCl) | 0.5 | 0.5 | 0.5 | 0.5 | 0.5 | 0.5 | 0.5 | 0.5 |
| Casein hydrolysate | 20 | — | — | — | — | — | — | — |
| Yeast extract | 10 | — | — | — | — | — | — | — |
| Thioglycollate medium | 5 | — | — | — | — | — | — | — |
| Hy-Pea ™ 7404 | 10 | 5 | 5 | — | — | 10 | 10 | 5 |
| UltraPep ™ Cotton | 10 | 5 | 5 | 10 | 6.667 | 10 | — | 5 |
| HyPep ™ 7504 | 10 | 5 | 5 | 10 | 6.667 | — | — | 5 |
| HyPep ™ 4601N | 10 | 5 | 5 | — | 6.667 | — | 10 | 5 |
| K$_2$HPO$_4$ | 5.5 | 5.5 | 5.5 | 5.5 | 5.5 | 5.5 | 5.5 | 5.5 |
| Na$_2$HPO$_4$ | 3 | 3 | 3 | 3 | 3 | 3 | 3 | 3 |
| OD 24 hr | 540 nm | 3.425 | 3.640 | 2.349 | 2.581 | 3.272 | 1.289 | 3.514 |
| | 600 nm | 2.969 | 3.159 | 2.029 | 2.244 | 1.096 | 1.096 | 3.032 |
| OD 48 hr | 540 nm | 0.769 | 0.836 | 1.633 | 0.961 | 1.501 | 1.148 | 0.803 |
| | 600 nm | 0.675 | 0.732 | 1.420 | 0.854 | 1.270 | 0.982 | 0.698 |

TABLE 10-continued

| Components of Medium | 8 (APF Medium Candidate) | 9 (APF Medium Candidate) | 10 (APF Medium Candidate) | 11 (APF Medium Candidate) | 12 (APF Medium Candidate) | 13 (APF Medium Candidate) | medium that is in current use |
|---|---|---|---|---|---|---|---|
| Glucose | 10 | 10 | 10 | 10 | 10 | 10 | 10 |
| Sodium Chloride (NaCl) | 0.5 | 0.5 | 0.5 | 0.5 | 0.5 | 0.5 | — |
| Casein hydrolysate | — | — | — | — | — | — | 20 |
| Yeast extract | — | — | — | — | — | — | 10 |
| Thioglycollate medium | — | — | — | — | — | — | 5 |
| Hy-Pea™ 7404 | 20 | — | 6.667 | 10 | 10 | 10 | — |
| UltraPep™ Cotton | — | — | — | 10 | 10 | 10 | — |
| HyPep™ 7504 | — | — | 6.667 | 10 | 10 | 10 | — |
| HyPep™ 4601N | — | 20 | 6.667 | 10 | 10 | 10 | — |
| K$_2$HPO$_4$ | 5.5 | 5.5 | 5.5 | 5.5 | 5.5 | 5.5 | — |
| Na$_2$HPO$_4$ | 3 | 3 | 3 | 3 | 3 | 3 | — |
| OD 24 hr | 0.776 | 1.257 | 3.457 | 5.376 | 5.235 | 4.809 | 2.208 |
|  | 0.649 | 1.098 | 2.950 | 4.689 | 4.534 | 4.246 | 1.863 |
| OD 48 hr | 0.880 | 1.278 | 0.962 | 1.986 | 1.994 | 2.010 | 3.185 |
|  | 0.744 | 1.124 | 0.818 | 1.708 | 1.710 | 1.717 | 2.708 |

Figure 9A:
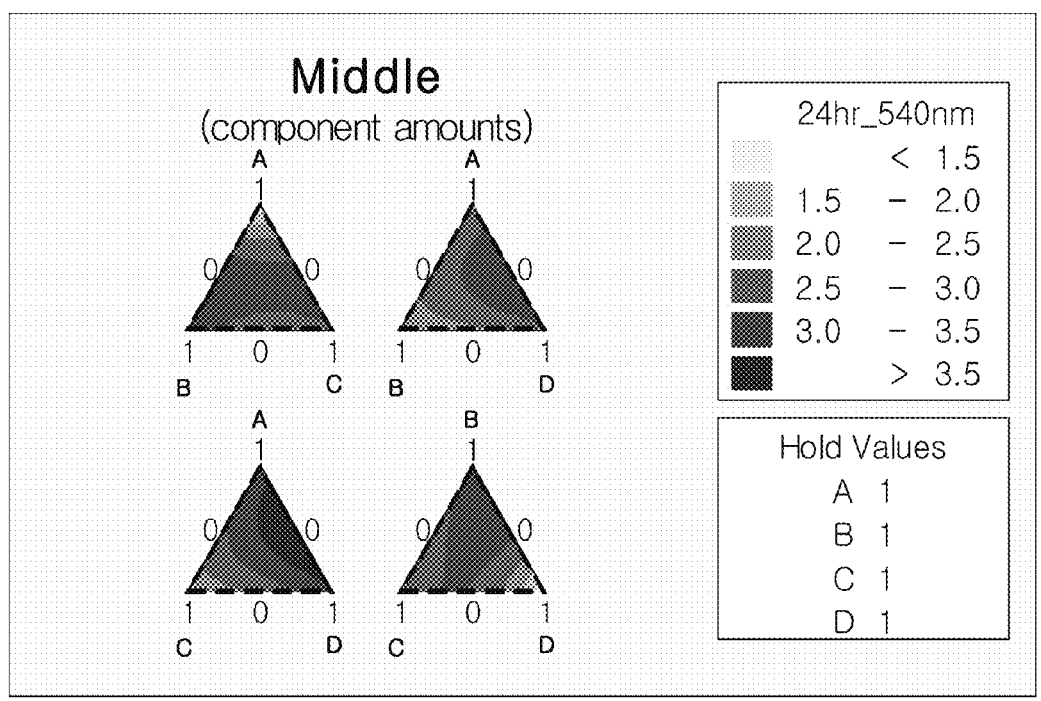
FIG. 9a contour plot for middle setting.
Figure 9B:
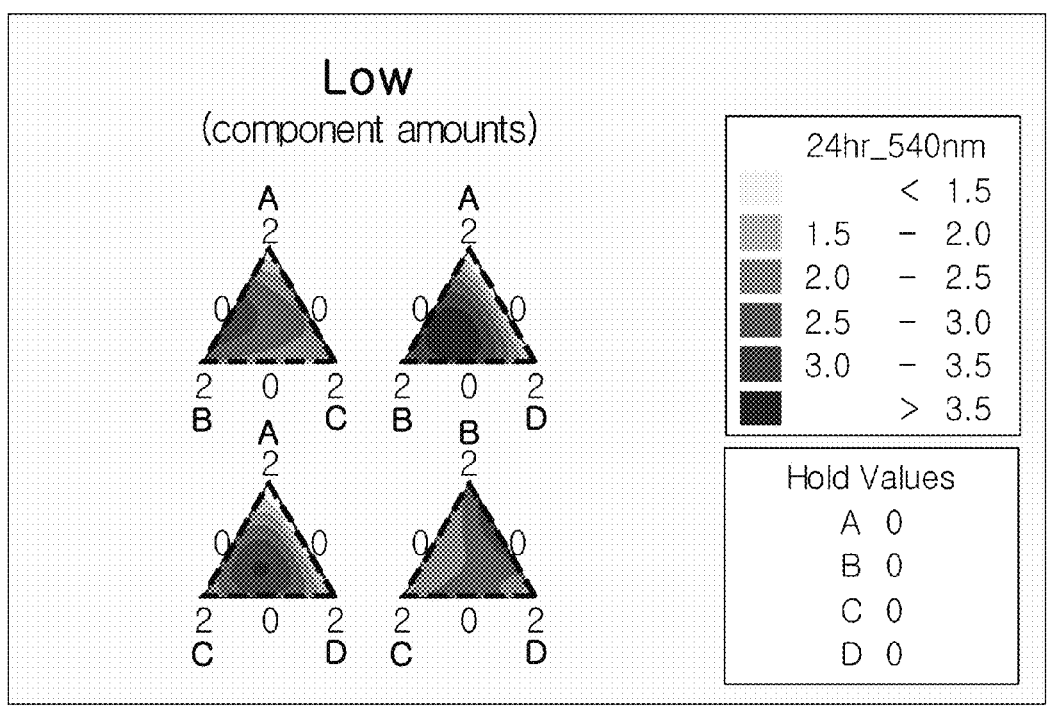
FIG. 9b contour plot for low setting.
Figure 9C:
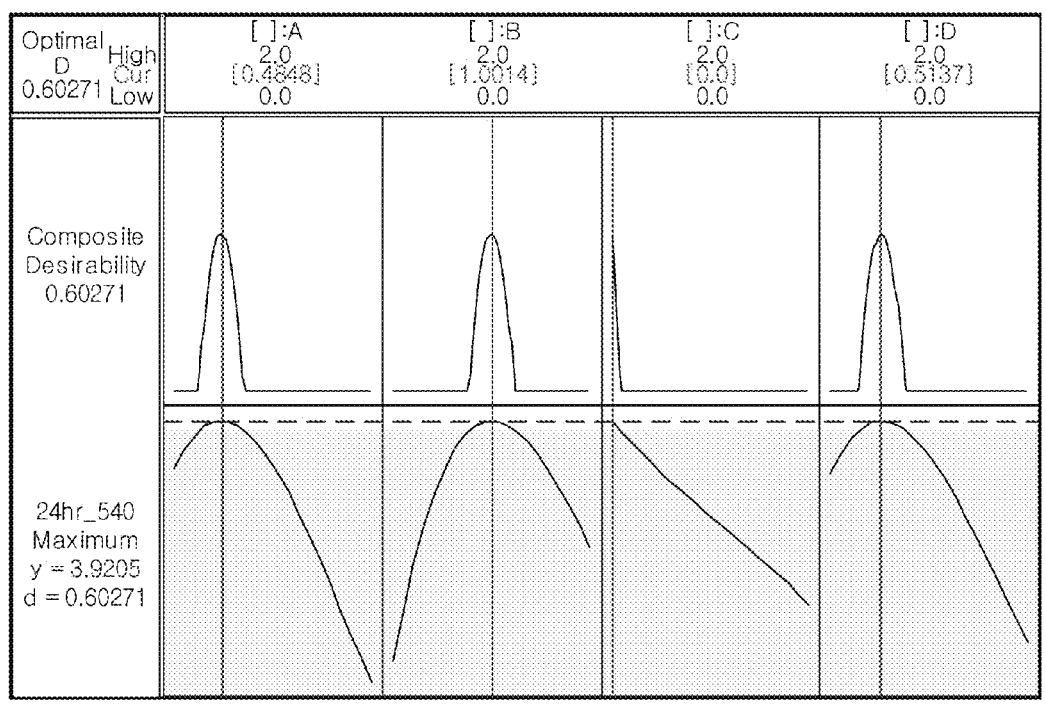
FIG. 9c response optimization for maximum OD.

As a result, as shown in FIGS. 9a to 9c, contour plots were drawn and used for analysis. It was determined that HyPep™ 7504 corresponding to the component C has the lowest effect on the growth of *Clostridium botulinum*. Based on this determination, HyPep™ 7504 was excluded from medium components. In conclusion, it was determined that the composition of the finally selected plant-derived peptones that are contained in the medium comprises 5 g/L Hy-Pea™ 7404, 10 g/L UltraPep™ Cotton and 5 g/L HyPep™ 4601N.

Example 9: Culture of *Clostridium botulinum* in Medium Containing or not Containing Nacl The medium compositions used in Examples 1 to 8 contained a small amount (0.5 g/L) of NaCl. In order to examine the growth of *Clostridium botulinum* according to the concentration change of NaCl, the content of NaCl in the medium was adjusted to a range from 0 to 1 g/L, followed by culture of the bacterium in the medium.

Table 11 shows the components of NaCl-containing media for culture of *Clostridium botulinum* and the growth of *Clostridium botulinum* in the media.

As a result, as shown in Table 11, there was no difference in the growth of the bacterium whether the medium contained NaCl or not. Thus, NaCl was excluded from the final APF medium components.

Example 10: Measurement of Growth Pattern of *Clostridium botulinum* in Finally Selected APF Medium and Toxin Concentration

*Clostridium botulinum* was inoculated into the finally selected *Clostridium botulinum* culture medium (10 g/L glucose, 5 g/L Hy-Pea™ 7404, 10 g/L UltraPep™ Cotton, 5 g/L HyPep™ 4601N, 5.5 g/L K$_2$HPO$_4$, and 3 g/L Na$_2$HPO$_4$) determined based on the results of Examples 1 to 9, and then the growth pattern of the bacterium and the toxin concentration were measured.

Table 12 shows the time-dependent OD value and the toxin concentration of *Clostridium botulinum* grown in the finally selected APF medium.

TABLE 11

| Components of Medium | g/L | 1 (APF Medium Candidate) | 2 (APF Medium Candidate) | 3 (APF Medium Candidate) | 4 (APF Medium Candidate) | 5 (APF Medium Candidate) | 6 (APF Medium Candidate) | 7 (APF Medium Candidate) | 8 (APF Medium Candidate) | 9 (APF Medium Candidate) |
|---|---|---|---|---|---|---|---|---|---|---|
| Glucose | 10 | 10 | 10 | 10 | 10 | 10 | 10 | 10 | 10 | 10 |
| Sodium Chloride (NaCl) | 0.5 | — | — | — | 0.5 | 0.5 | 0.5 | 1 | 1 | 1 |
| Hy-Pea™ 7404 | 5 | 5 | 5 | 5 | 5 | 5 | 5 | 5 | 5 | 5 |
| UltraPep™ Cotton | 10 | 10 | 10 | 10 | 10 | 10 | 10 | 10 | 10 | 10 |
| HyPep™ 4601N | 5 | 5 | 5 | 5 | 5 | 5 | 5 | 5 | 5 | 5 |
| K$_2$HPO$_4$ | 5.5 | 5.5 | 5.5 | 5.5 | 5.5 | 5.5 | 5.5 | 5.5 | 5.5 | 5.5 |
| Na$_2$HPO$_4$ | 3 | 3 | 3 | 3 | 3 | 3 | 3 | 3 | 3 | 3 |
| OD 24 hr | 540 nm | 2.166 | 2.154 | 2.151 | 2.148 | 2.115 | 2.120 | 2.145 | 2.147 | 2.140 |
|  | 600 nm | 1.940 | 1.923 | 1.922 | 1.922 | 1.892 | 1.896 | 1.919 | 1.922 | 1.917 |

TABLE 12

| Time of Culture (hr) | OD 540 nm | OD 600 nm | Toxin Conc. in Supernatant (µg/ml) | Total Toxin Conc. after rupturing strain (µg/ml) |
|---|---|---|---|---|
| 0 | 0 | 0 | 0 | 0 |
| 6 | 0.0953 | 0.0393 | 0.00 | 0.00 |
| 9 | 0.0648 | 0.0525 | 0.00 | 0.00 |
| 12 | 0.5003 | 0.4411 | 0.00 | 0.00 |
| 14 | 1.1328 | 0.9958 | 2.18 | 2.04 |
| 16 | 1.6252 | 1.4484 | 4.64 | 10.22 |
| 18 | 2.3435 | 2.0215 | 6.77 | 18.15 |
| 20 | 2.777 | 2.4015 | 8.47 | 29.26 |
| 22 | 3.3485 | 2.896 | 9.46 | 31.86 |
| 24 | 3.5465 | 3.0695 | — | 31.73 |
| 28 | 3.452 | 2.982 | — | 37.31 |
| 36 | 2.5955 | 2.242 | 21.20 | 38.00 |
| 48 | 0.792 | 0.7224 | 31.41 | 38.39 |

Figure 10:
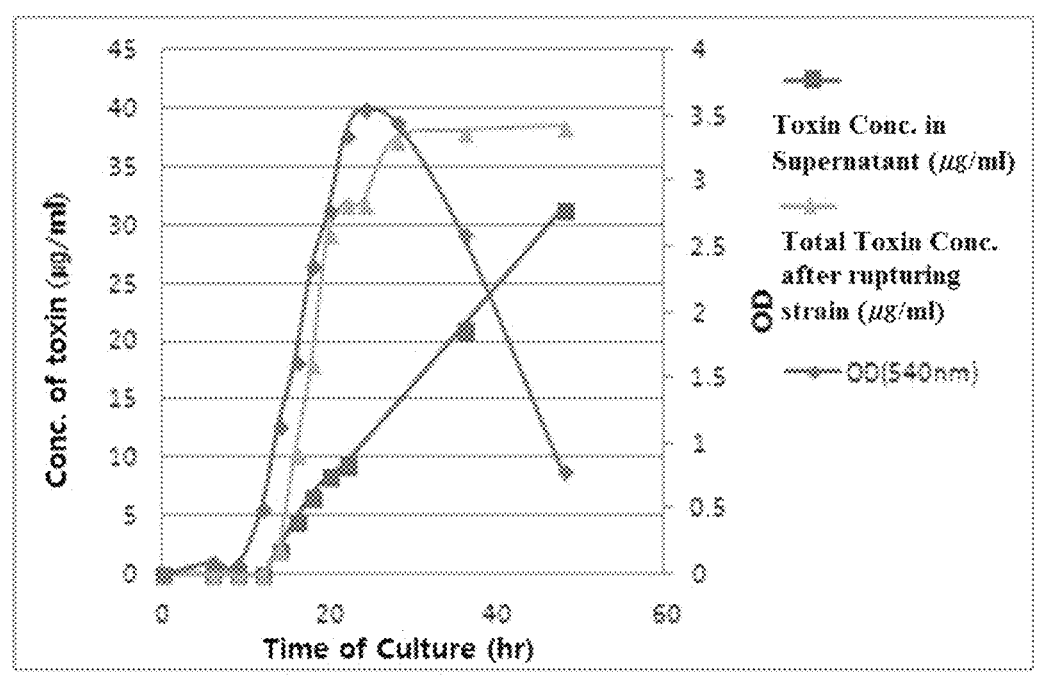
FIG. 10 shows the growth curve of *Clostridium botulinum* in the finally selected APF medium, and a change in toxin concentration.

As a result, as shown in Table 12 and FIG. 10, the OD value started to increase after 12 hours of culture of *Clostridium botulinum*, and at 24 hours of culture, the culture medium showed an $OD_{540nm}$ of 3.5465 and an $OD_{600nm}$ of 3.0695. Then, the OD value decreased gradually, and at 48 hours of culture, the culture medium showed an $OD_{540nm}$ of 0.792 and an $OD_{600nm}$ of 0.7224. The toxin concentration in the supernatant of *Clostridium botulinum* started to increase after 14 hours of culture and showed a final value of 31.41 µg/ml. When the toxin concentration was measured after rupturing the bacterium, the toxin started to be produced after 5 hours of culture, and the toxin concentration continued to increase, was maintained at a uniform level after 28 hours of culture, and showed a final value of 38.39 µg/ml.

In conclusion, the finally selected APF (animal protein-free medium) composition determined based on the results of Examples 1 to 10 is summarized in Table 13.

TABLE 13

| Components of Medium | | g/L |
|---|---|---|
| Carbon Source | Glucose | 10 |
| Nitrogen Source | Hy-Pea ™ 7404 | 5 |
| | UltraPep ™ Cotton | 10 |
| (Vegetable Peptone) | HyPea ™ 4601N | 5 |
| Mineral | $K_2HPO_4$ | 5.5 |
| | $Na_2HPO_4$ | 3 |

Example 11: Selection of Medium Composition Containing Plant-Derived Peptones and Casein Hydrolysate The APF medium composition determined based on the results of Examples 1 to 10 showed an increased growth rate of the bacterium compared to the medium that is in current use (original medium), but the addition of a medium component that further increases the growth rate of the bacterium while having no risk of infection with TSE or the like was taken into consideration. As a result, a TSE-free casein hydrolysate (e.g., TSE-certificated casein hydrolysate) was added to the APF medium, and the growth of the bacterium in the medium was examined.

One or two TSE-free casein hydrolysates were added to the APF medium determined based on the results of Examples 1 to 10. Specifically, *Clostridium botulinum* was cultured in medium A (obtained by adding the casein hydrolysate N-Z-Amine A to the medium composition containing the plant-derived peptones), or medium B (obtained by adding N-Z-Case TT to the medium composition), or medium C (obtained by adding casamino acid to the medium composition), or medium D (obtained by adding tryptone to the medium composition) for 24 hours and 48 hours, and the growth of the bacterium was examined by measuring the OD (540 nm, 600 nm) values during the culture (Table 14). In addition, the results of the measurement were subjected to statistical analysis using statistical program, thereby selecting a medium composition showing the highest growth at 24 hours of culture of the bacterium.

Table 14 shows the results of the time-dependent growth of *Clostridium botulinum* in the medium compositions containing the casein hydrolysates in addition to the plant-derived peptones.

TABLE 14

| | | A | B | C | D | OD at 24 hr | | OD at 48 hr | |
|---|---|---|---|---|---|---|---|---|---|
| StdOrder | RunOrder | (N-Z-AMINE A) | (N-Z-CASE TT) | (Casamino acid) | (Tryptone) | 540 nm | 600 nm | 540 nm | 600 nm |
| 1 | 11 | 2 | 0 | 0 | 0 | 4.7040 | 4.0620 | 2.3385 | 2.0715 |
| 2 | 6 | 0 | 2 | 0 | 0 | 4.8460 | 4.1540 | 1.2785 | 1.1525 |
| 3 | 2 | 0 | 0 | 2 | 0 | 4.7470 | 4.1140 | 1.7340 | 1.5510 |
| 4 | 10 | 0 | 0 | 0 | 2 | 4.5240 | 3.8620 | 1.1890 | 1.0710 |
| 5 | 4 | 1 | 1 | 0 | 0 | 5.1810 | 4.4540 | 1.5360 | 1.3720 |
| 6 | 3 | 1 | 0 | 1 | 0 | 4.9620 | 4.2900 | 2.0780 | 1.8460 |
| 7 | 13 | 1 | 0 | 0 | 1 | 4.7280 | 4.0700 | 1.2785 | 1.1475 |
| 8 | 9 | 0 | 1 | 1 | 0 | 4.8410 | 4.1700 | 1.5390 | 1.3735 |
| 9 | 7 | 0 | 1 | 0 | 1 | 4.8060 | 4.1370 | 1.2260 | 1.1075 |
| 10 | 15 | 0 | 0 | 1 | 1 | 4.5690 | 3.9220 | 1.3800 | 1.2375 |
| 11 | 1 | 0.666666667 | 0.666666667 | 0.666666667 | 0 | 5.3350 | 4.5990 | 1.5385 | 1.3880 |
| 12 | 14 | 0.666666667 | 0.666666667 | 0 | 0.666666667 | 4.9790 | 4.2880 | 1.3570 | 1.2035 |
| 13 | 5 | 0.666666667 | 0 | 0.666666667 | 0.666666667 | 4.9020 | 4.2160 | 1.7280 | 1.5575 |
| 14 | 8 | 0 | 0.666666667 | 0.666666667 | 0.666666667 | 4.9930 | 4.2820 | 1.5305 | 1.3670 |
| 15 | 12 | 0.5 | 0.5 | 0.5 | 0.5 | 4.8500 | 4.1860 | 1.4845 | 1.3250 |

Figure 11A:
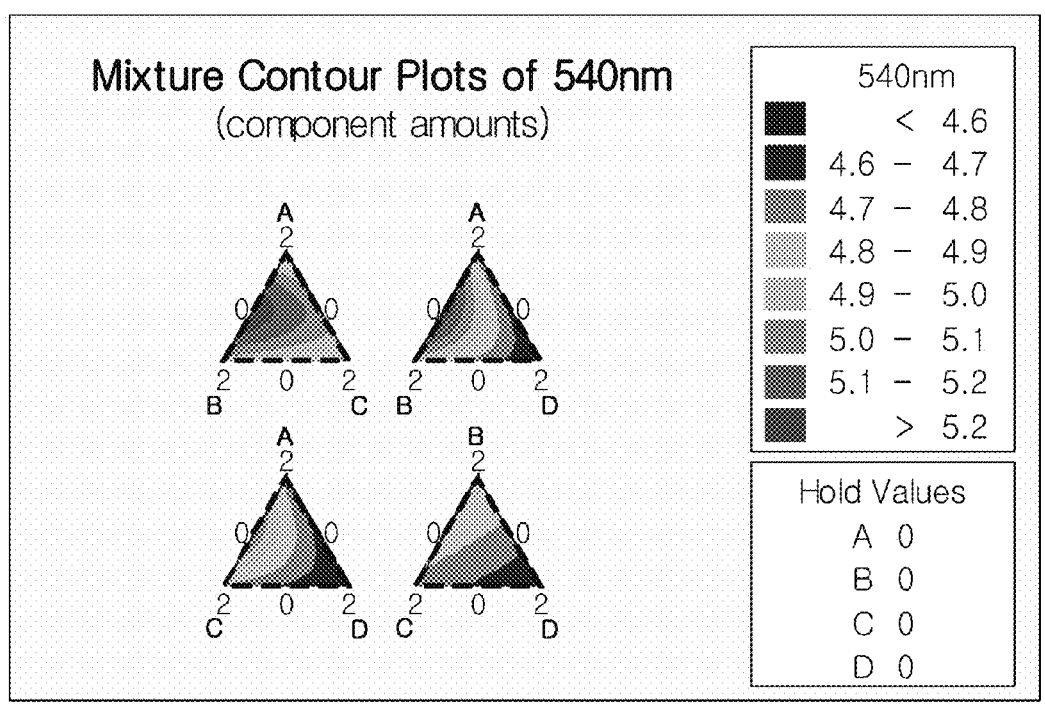
FIG. 11a contour plot for lower setting.
Figure 11B:
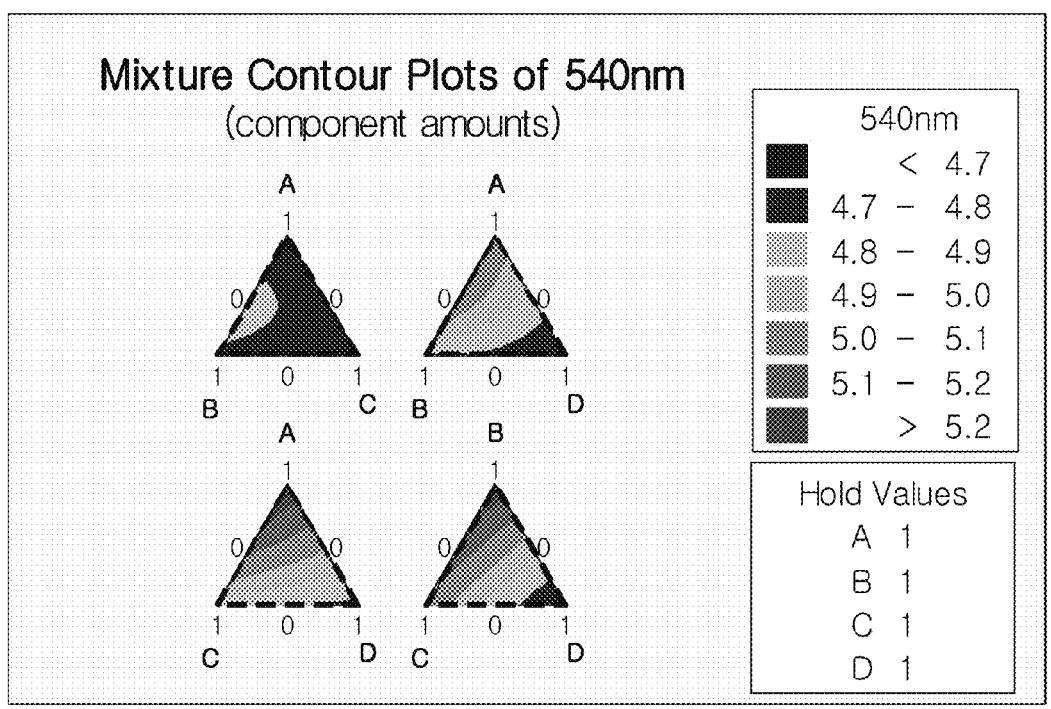
FIG. 11b contour plot for middle setting.
Figure 12:
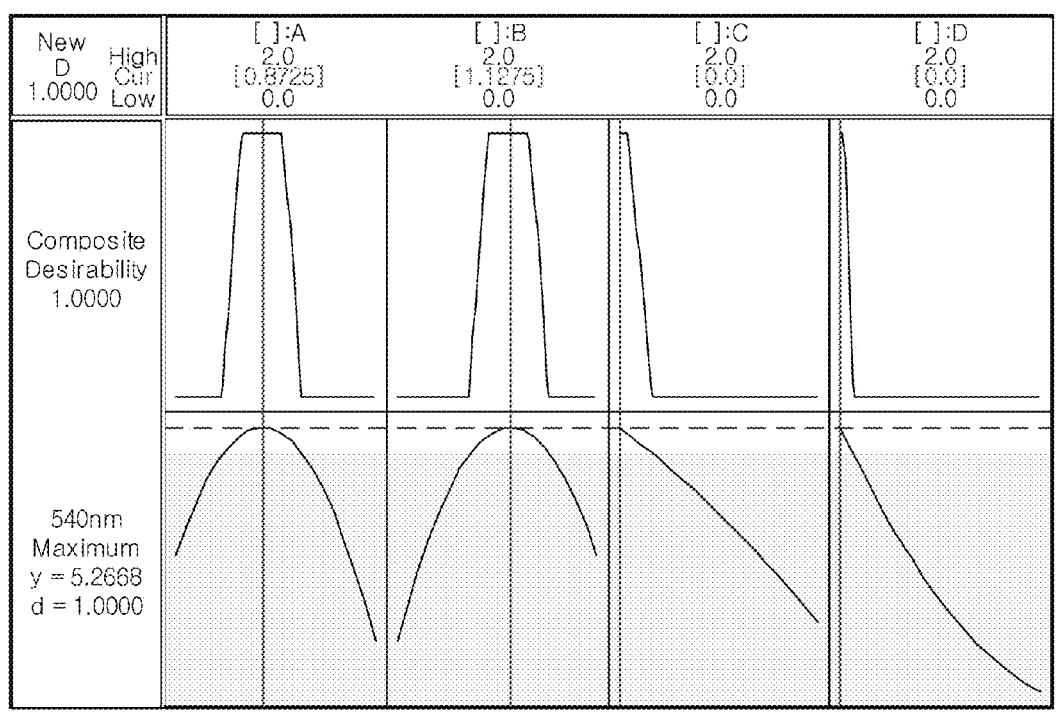
FIG. 12 shows response optimization for a culture medium at 24 hours after inoculation of *Clostridium botulinum* into a medium comprising plant-derived peptone to which a casein hydrolysate has been added.

Meanwhile, as shown in FIGS. 11a to 11b, in order to find conditions showing the highest growth at 24 hours of culture of the bacterium, mixture contour plots for lower bound setting and middle setting conditions were drawn. As a result, it could be seen that *Clostridium botulinum* showed the highest growth in the region in which medium A and medium B exist and medium C and medium D show a value of 0. In addition, as shown in FIG. 12, conditions showing the highest growth of the bacterium were investigated, and as a result, it was shown that the bacterium showed the highest growth under the following conditions: A=0.8725, B=1.1275, C=0, and D=0. Based on such results, medium A (N-Z-Amine A) and medium B (N-Z-Case TT) were finally selected from among the four medium components.

Example 12: Final Selection of Concentration of Medium Containing Plant-Derived Peptones and Casein Hydrolysate To determine optimal medium composition for the two casein hydrolysate medium components selected in Example 11, a response surface experiment was performed with a CCF (central composite faced) design.

Table 15 shows the results of analyzing the time-dependent growth of *Clostridium botulinum* in the medium composition containing the plant-derived peptones and the casein hydrolysates using the CCF response surface methodology.

TABLE 15

| | | A | B | OD at 24 hr | | OD at 48 hr | |
|---|---|---|---|---|---|---|---|
| StdOrder | RunOrder | (N-Z-AMINE A) | (N-Z-CASE TT) | 540 nm | 600 nm | 540 nm | 600 nm |
| 1 | 3 | 0 | 0 | 3.4850 | 2.9430 | 1.4095 | 1.2110 |
| 2 | 2 | 2 | 0 | 5.1410 | 4.4030 | 2.3800 | 2.0880 |
| 3 | 8 | 0 | 2 | 5.1410 | 4.4020 | 1.3590 | 1.1415 |
| 4 | 7 | 2 | 2 | 5.2690 | 4.5560 | 1.7715 | 1.5420 |
| 5 | 11 | 0 | 1 | 4.2000 | 3.5680 | 0.6885 | 0.6075 |
| 6 | 10 | 2 | 1 | 5.3730 | 4.6280 | 1.7055 | 1.4930 |
| 7 | 5 | 1 | 0 | 3.9240 | 3.3190 | 3.2370 | 2.8775 |
| 8 | 13 | 1 | 2 | 5.1380 | 4.4140 | 1.2905 | 1.1330 |
| 9 | 12 | 1 | 1 | 5.1850 | 4.4520 | 1.5585 | 1.3380 |
| 10 | 6 | 1 | 1 | 5.3810 | 4.6390 | 2.9825 | 2.6300 |
| 11 | 9 | 1 | 1 | 4.9080 | 4.2150 | 0.8165 | 0.7125 |
| 12 | 1 | 1 | 1 | 5.1150 | 4.3910 | 1.4515 | 1.2725 |
| 13 | 4 | 1 | 1 | 5.2110 | 4.4710 | 2.6785 | 2.3405 |

As a result, as shown in Table 15, it was found that *Clostridium botulinum* grew.

Figure 13:
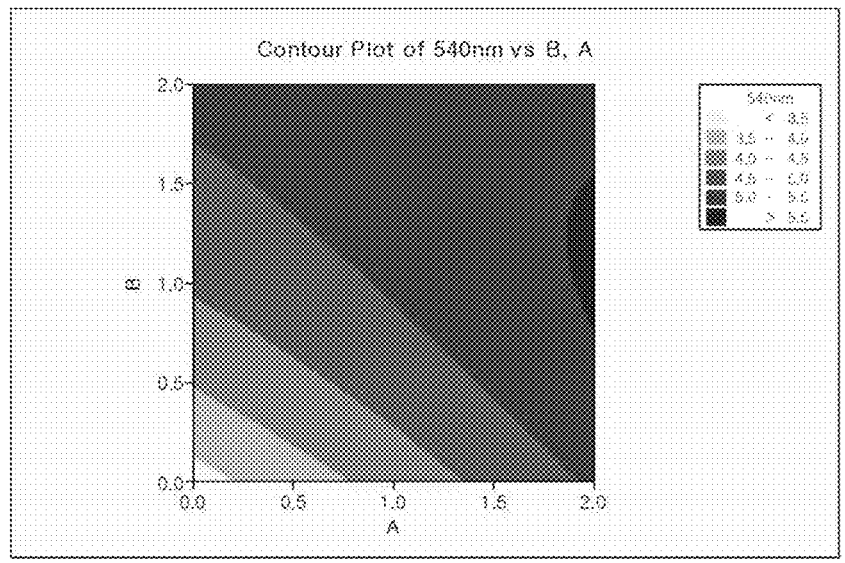
FIG. 13 shows contour plots of a CCF (central composite faced) design. (A) plot of statistical program; and (B) plot of statistical program.
Figure 13:
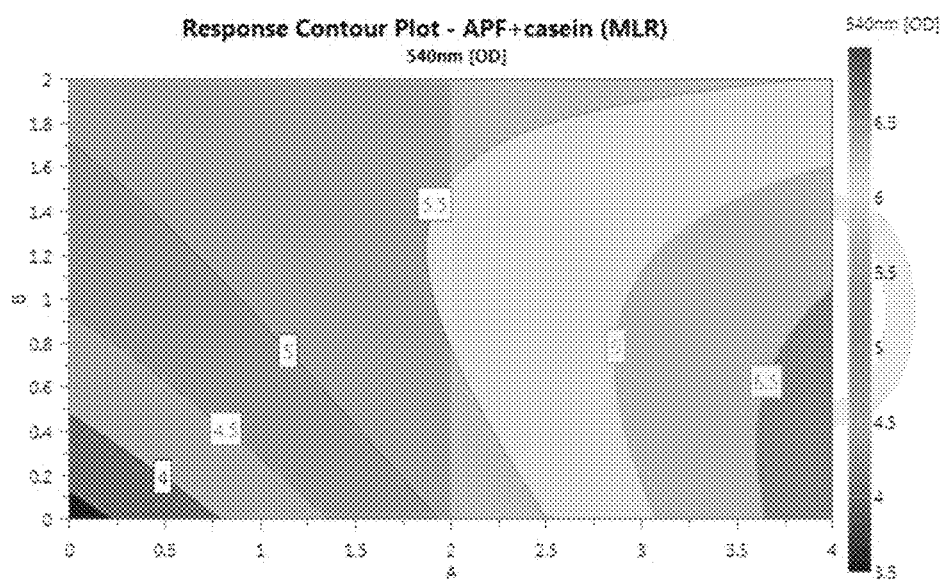
Figure 14:
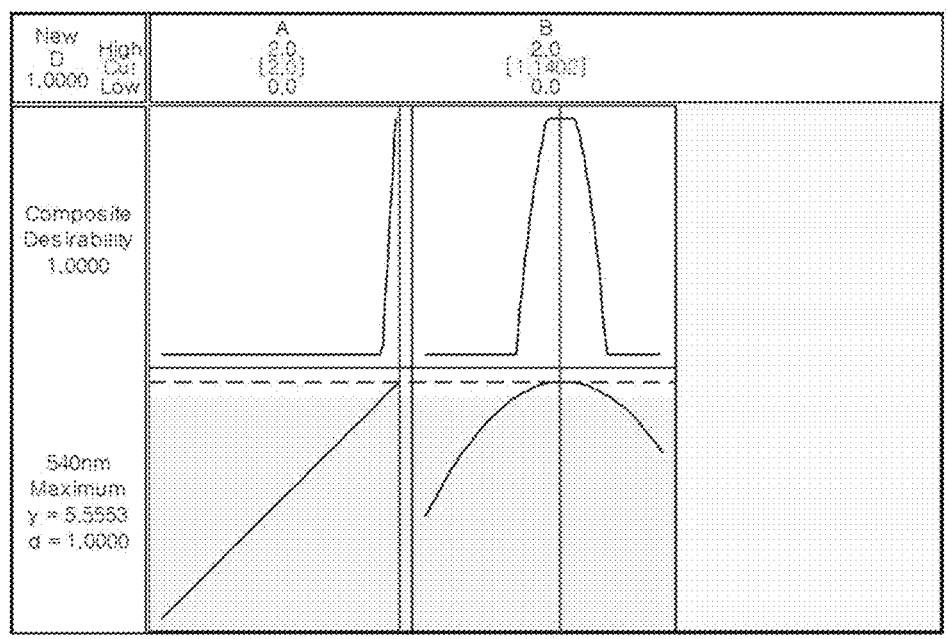
FIG. 14 shows contour plots (A) of a CCF (central composite faced) design, and a optimization plot (B).

Meanwhile, a contour plot of a model set using statistical program was drawn. As shown in FIG. 13 (A), the medium component A increased outside the experimental range, indicating that there are optimal conditions. To confirm it, the range of the medium component A (N-Z-Amine A) was extended outside the experimental range using statistical program, and a contour plot was drawn. As a result, as shown in FIG. 13(B), the growth of the bacterium increased as the concentration of the medium component A increased. However, because an increase in the content of the casein hydrolysate can cause a problem in terms of solubility, an optimal condition was selected within the experimental ranges.

As a result, the bacterium showed the highest growth at 24 hours of culture under the following conditions: A=2.0, and B=1.1402. Based on such results, a medium composition containing the casein hydrolysate added to the animal protein-free (APF) medium, which shows the highest growth of *Clostridium botulinum*, was determined as shown in Table 16.

TABLE 16

| Components of Medium | | g/L |
|---|---|---|
| Carbon Source | Glucose | 10 |
| Nitrogen Source | Hy-Pea ™ 7404 | 5 |

TABLE 16-continued

| Components of Medium | | g/L |
|---|---|---|
| (Vegetable Pepton) | UltraPep ™ Cotton | 10 |
| | HyPea ™ 4601N | 5 |
| Mineral | $K_2HPO_4$ | 5.5 |
| | $Na_2HPO_4$ | 3 |
| Nitrogen Source (Casein Hydrolysate) | N-Z-AMINE A | 20 |
| | N-Z-CASE TT | 11 |

Example 13: Growth Pattern of *Clostridium botulinum* in Medium Containing Plant-Derived Peptones and Casein Hydrolysates Using the medium composition containing plant-derived peptones and/or casein hydrolysates, determined based on the results of Examples 1 to 10, *Clostridium botulinum* was cultured, and the growth pattern of the bacterium was examined.

Table 17 shows time-dependent OD values of the growth of *Clostridium botulinum* between a medium that is in current use, a plant-derived peptone-containing medium (APF medium), and a final medium containing plant-derived peptones and casein hydrolysates (APF medium+casein).

TABLE 17

| Time of Culture | medium that is in current use | | APF Medium | | APF Medium + Casein | |
|---|---|---|---|---|---|---|
| (hr) | 540 nm | 600 nm | 540 nm | 600 nm | 540 nm | 600 nm |
| 0 | 0 | 0 | 0 | 0 | 0 | 0 |
| 10 | 0 | 0 | 0 | 0 | 0 | 0 |
| 12 | 0 | 0 | 0 | 0 | 0 | 0 |
| 15 | 0.0084 | 0.0059 | 0.2064 | 0.1821 | 0.7156 | 0.6551 |
| 18 | 0.073 | 0.608 | 1.0552 | 0.9296 | 2.8395 | 2.5015 |
| 21 | 0.4952 | 0.4204 | 1.85 | 1.5895 | 4.545 | 3.92 |
| 24 | 1.2382 | 0.9954 | 2.8595 | 2.472 | 5.244 | 4.551 |
| 26 | 2.608 | 2.215 | 3.4745 | 3.009 | 5.628 | 4.786 |
| 28 | 2.8335 | 2.416 | 3.526 | 2.994 | 5.188 | 4.489 |
| 36 | 3.324 | 2.838 | 3.361 | 2.911 | 3.838 | 3.396 |
| 39 | 3.384 | 2.894 | 2.9255 | 2.5185 | 3.7225 | 3.2945 |
| 44 | 3.1105 | 2.6415 | 1.968 | 1.712 | 2.9725 | 2.778 |
| 60 | 2.1484 | 1.8164 | 0.76 | 0.684 | 1.9788 | 1.7564 |

Figure 15:
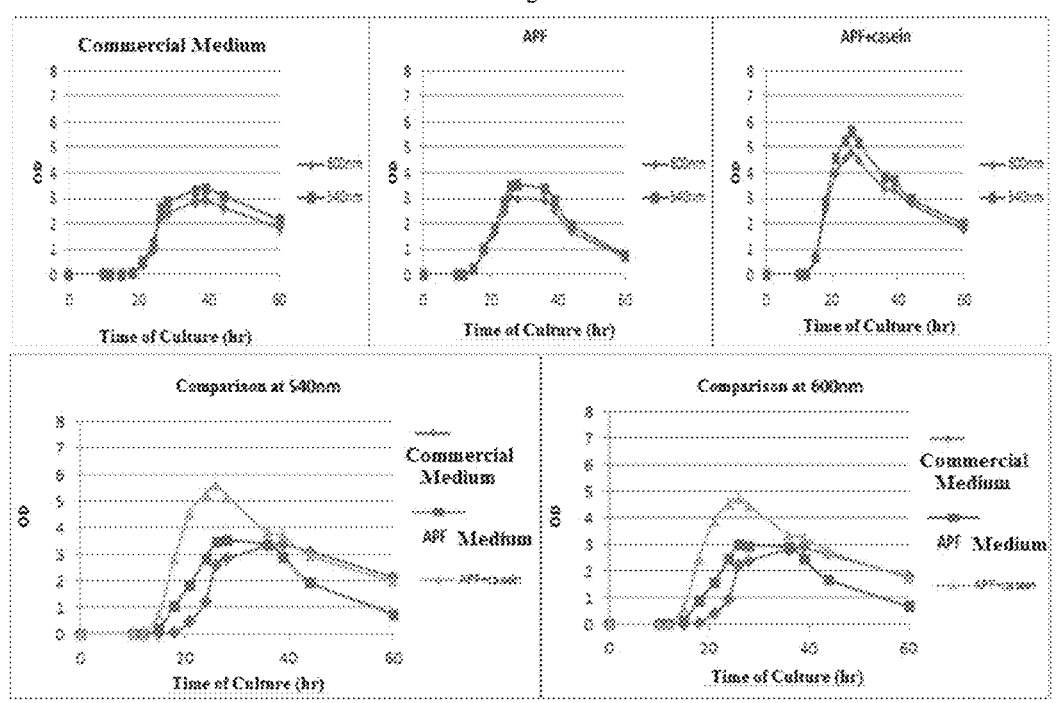
FIG. 15 is a set of graphs showing time-dependent OD values indicating the growth of *Clostridium botulinum* in a medium that is in current use, a medium comprising plant-derived peptones and a medium comprising plant-derived peptones and casein hydrolysate.

As a result, as shown in Table 17 and FIG. 15, the medium that is in current use showed an increase in the growth rate after 24 hours of culture of *Clostridium botulinum* and showed the peak $OD_{540nm}$ value of 3.384 at 39 hours of culture. The APF medium containing plant-derived peptones showed an increase in the growth rate after 18 hours of culture and showed a peak $OD_{540nm}$ value of 3.526 at 28 hours of culture.

In addition, the plant-derived peptone-containing APF medium+casein hydrolysate showed an increase in the growth rate after 18 hours of culture and showed a peak $OD_{540nm}$ value of 5.628 at 26 hours of culture. When the $OD_{540nm}$ value at 24 hours of culture was compared, the medium that is in current use showed an $OD_{540nm}$ value of 1.2382, the plant-derived peptone-containing APF medium showed an $OD_{540nm}$ value of 2.8595, and the plant-derived peptone-containing APF medium+casein hydrolysate showed an $OD_{540nm}$ value of 5.244. Thus, the OD value of the plant-derived peptone-containing APF medium+casein hydrolysate at 24 hours of culture was about 4.23 times higher than that of the medium that is in current use and about 1.83 times higher than that of the plant-derived peptone-containing APF medium. Moreover, the peak OD value of the plant-derived peptone-containing APF medium+casein hydrolysate was about 1.6 times higher than that of the plant-derived peptone-containing APF medium.

INDUSTRIAL APPLICABILITY

As described above, when the medium according to the present invention, which contains plant-derived peptone, casein hydrolysate and mineral, is used for culture of *Clostridium botulinum*, the growth rate of the bacterium in the medium is higher than that in each of the medium that is in current use and the medium containing plant-derived peptone alone. In addition, when the medium of the present invention is used, a high concentration of botulinum toxin can be produced by culturing the bacterium in a safe manner.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A medium composition for culture of *Clostridium botulinum*, the medium composition comprising:
   plant-derived peptones comprising a garden pea hydrolysate, a cotton seed hydrolysate and a wheat gluten hydrolysate with a ratio of 1:0.68-14.46:0.09-9.87 by weight; and
   a casein hydrolysate.

2. The medium composition of claim 1, wherein the total content of the plant-derived peptones in said medium is comprised with content of 0.1-10% (w/v).

3. The medium composition of claim 1, wherein the casein hydrolysate is comprised in the medium composition with content of 0.22-15.5% (w/v).

4. The medium composition of claim 1, wherein the plant-derived peptone or the casein hydrolysate is subjected to an enzyme treatment.

5. The medium composition of claim 1, further comprising a carbon source, and at least one mineral selected from the group consisting of $K_2HPO_4$ (dipotassium phosphate), $Na_2HPO_4$ (disodium phosphate) and $KH_2PO_4$ (monopotassium phosphate).

6. The medium composition of claim 5, wherein the mineral is comprised in the medium composition with content of 0.05-3.5% Lw/v).

7. A method for producing botulinum toxin, comprising the steps of:
   (a) culturing *Clostridium botulinum* using the medium composition of claim 1 to produce botulinum toxin; and
   (b) recovering the produced botulinum toxin.

8. The method of claim 7, wherein the culture is performed under anaerobic conditions.

9. The method of claim 7, wherein the botulinum toxin is selected from the group consisting of botulinum toxin serotypes A, B, C, D, E, F and G.

\* \* \* \* \*

UNITED STATES PATENT AND TRADEMARK OFFICE
CERTIFICATE OF CORRECTION

PATENT NO. : 10,117,927 B2  
APPLICATION NO. : 15/521833  
DATED : November 6, 2018  
INVENTOR(S) : Kyoung-Yun Kim Page 1 of 1

It is certified that error appears in the above-identified patent and that said Letters Patent is hereby corrected as shown below:

On the Title Page

Right-hand column, under "Other Publications", in the third reference listing beginning with "Fang et al. 2009..." and ending with "...(Year: 2009)*", in Line 2 thereof, after "both animal and dairy proteins", the word "of" should be -- or --.

In the Claims

Column 30, Line 27, in Claim 6, Line 3, "Lw/v)" should be -- "(w/v) --.

Signed and Sealed this  
Eleventh Day of December, 2018

Andrei Iancu  
*Director of the United States Patent and Trademark Office*